United States Patent
Upadhye et al.

(10) Patent No.: US 9,440,927 B2
(45) Date of Patent: Sep. 13, 2016

(54) PROCESS FOR PREPARATION OF SUBSTITUTED 3'-HYDROAZINO-DIPHENYL-3-CARBOXYLIC ACID COMPOUNDS

(75) Inventors: Bhargav Krishnaji Upadhye, Aurangabad (IN); Shivaji Eknath Jagadale, Kalyan (IN); Mukesh Soni, Ajmer (IN)

(73) Assignee: Glenmark Pharmaceuticals Limited, Mumbai (IN)

( * ) Notice: Subject to any disclaimer, the term of this patent is extended or adjusted under 35 U.S.C. 154(b) by 203 days.

(21) Appl. No.: 14/344,393

(22) PCT Filed: Sep. 12, 2012

(86) PCT No.: PCT/IN2012/000610
§ 371 (c)(1),
(2), (4) Date: Nov. 5, 2014

(87) PCT Pub. No.: WO2013/072921
PCT Pub. Date: May 23, 2013

(65) Prior Publication Data
US 2015/0087845 A1    Mar. 26, 2015

(30) Foreign Application Priority Data

Sep. 13, 2011 (IN) .......................... 2570/MUM/2011
Oct. 17, 2011 (IN) .......................... 2898/MUM/2011
Mar. 5, 2012 (IN) ............................ 582/MUM/2012

(51) Int. Cl.
C07D 231/46 (2006.01)
C07C 251/76 (2006.01)

(52) U.S. Cl.
CPC ........... *C07D 231/46* (2013.01); *C07C 251/76* (2013.01)

(58) Field of Classification Search
CPC .................................................. C07D 231/46
See application file for complete search history.

(56) References Cited

U.S. PATENT DOCUMENTS

| 2,753,336 A | * | 7/1956 | Maderni | .................. | C09B 45/20 |
|---|---|---|---|---|---|
| | | | | | 534/700 |
| 7,160,870 B2 | | 1/2007 | Duffy et al. | | |
| 7,547,719 B2 | | 6/2009 | Moore | | |
| 7,786,159 B2 | * | 8/2010 | Spencer | ............... | C07D 231/46 |
| | | | | | 514/404 |
| 7,956,048 B2 | * | 6/2011 | Leksic | .................. | C07D 231/46 |
| | | | | | 514/150 |
| 8,022,093 B2 | * | 9/2011 | Leksic | .................. | C07D 231/46 |
| | | | | | 514/404 |
| 8,143,287 B2 | * | 3/2012 | Spencer | ............... | C07D 231/46 |
| | | | | | 514/326 |
| 2009/0076112 A1 | * | 3/2009 | Czarnik | ............... | C07D 231/46 |
| | | | | | 514/404 |
| 2010/0256212 A1 | * | 10/2010 | Leksic | .................. | C07D 231/46 |
| | | | | | 514/404 |
| 2012/0238612 A1 | * | 9/2012 | Leksic | .................. | C07D 231/46 |
| | | | | | 514/404 |

FOREIGN PATENT DOCUMENTS

| WO | 0189457 A2 | 11/2001 |
|---|---|---|
| WO | 03098992 A2 | 12/2003 |

OTHER PUBLICATIONS

Kumar, et al. "Exploration of Antimicrobial and Antioxidant Potential of Newly Synthesized 2,3-Disubstituted Quinazoline-4(3H)-Ones", Bioorganic & Medicinal Chemistry Letters, pp. 4353-4357 (2011).

* cited by examiner

*Primary Examiner* — Nyeemah A Grazier
(74) *Attorney, Agent, or Firm* — M. Carmen & Asssociates, PLLC

(57) ABSTRACT

The present invention provides a process for the preparation of substituted 3'-hydrazino-biphenyl-3-carboxylic acid compounds. The present invention further provides a process for the preparation of 3'-{N'-[1-(3,4-dimethylphenyl)-3-methyl-5-oxo-1,5-dihydro-pyrazol-4-ylidene]hydrazino}-2'-hydroxybiphenyl-3-carboxylic acid, its intermediate compounds and pharmaceutically acceptable salts thereof.

19 Claims, 2 Drawing Sheets

Glenmark Generics Limited

Glenmark Generics Limited

Glenmark Generics Limited

Glenmark Generics Limited

PROCESS FOR PREPARATION OF SUBSTITUTED 3'-HYDROAZINO-DIPHENYL-3-CARBOXYLIC ACID COMPOUNDS

PRIORITY

This application claims priority under 35 U.S.C. §371 to International Application No. PCT/IN2012/000610, filed Sep. 12, 2012 which claims the benefit to Indian Provisional Applications 2570/MUM/2011 filed on Sep. 13, 2011, 2898/MUM/2011 filed on Oct. 17, 2011 and 582/MUM/2012 filed on Mar. 5, 2012 entitled "PROCESS FOR PREPARATION OF SUBSTITUTED 3'-HYDRAZINO-BIPHENYL-3-CARBOXYLIC ACID COMPOUNDS", which are incorporated herein by reference.

BACKGROUND OF THE INVENTION

1. Technical Field

The present invention relates to a process for the preparation of substituted 3'-hydrazino-biphenyl-3-carboxylic acid compounds. The present invention relates to a process for the preparation of 3'-{N'-[1-(3,4-dimethylphenyl)-3-methyl-5-oxo-1,5-dihydro-pyrazol-4-ylidene]hydrazino}-2'-hydroxybiphenyl-3-carboxylic acid, its intermediate compounds and pharmaceutically acceptable salts thereof.

2. Description of the Related Art

Eltrombopag, also known as 3'-{N'-[1-(3,4-dimethylphenyl)-3-methyl-5-oxo-1,5-dihydro-pyrazol-4-ylidene]-hydrazino}-2'-hydroxybiphenyl-3-carboxylic acid is represented by the structure of formula Ia.

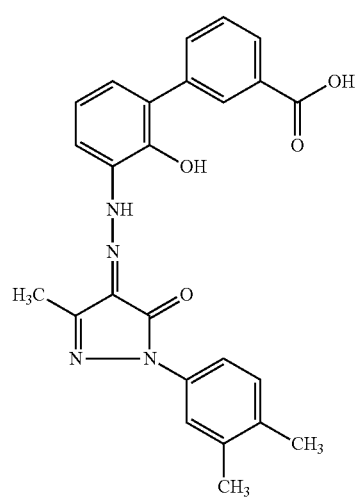

Ia

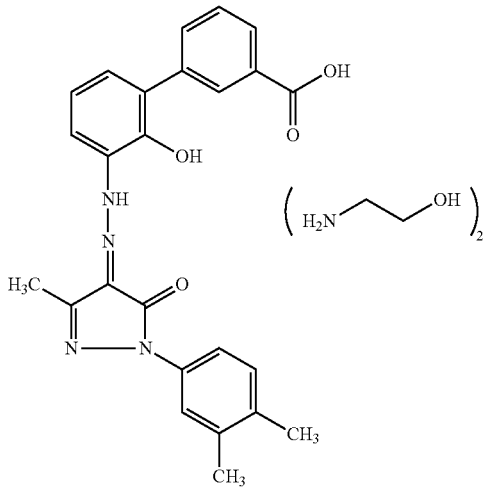

II

Eltrombopag olamine, compound of formula II, is a thrombopoietin receptor agonist indicated for the treatment of thrombocytopenia in patients with chronic immune (idiopathic) thrombocytopenic purpura who have had an insufficient response to corticosteroids, immunoglobulins, or splenectomy. Eltrombopag olamine is marketed under the brand name PROMACTA® in the United States (approved in November 2008) and under the brand name REVOLADE® in Europe (approved in March 2010).

Eltrombopag belongs to a class of substituted 3'-hydrazino-biphenyl-3-carboxylic acid compounds of formula I,

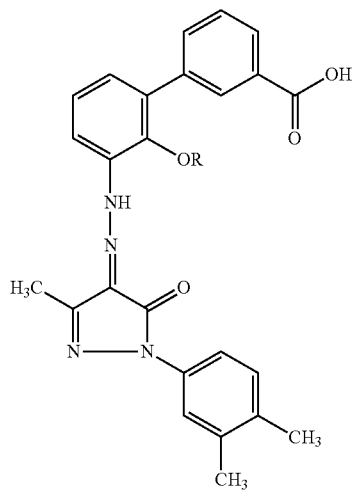

I

U.S. Pat. No. 7,160,870 (the '870 patent) discloses eltrombopag and its salts. U.S. Pat. No. 7,547,719 discloses eltrombopag olamine, bisethanolamine salt of eltrombopag. The '870 patent discloses a process for the preparation of eltrombopag as schematically represented by Scheme I.

Scheme I

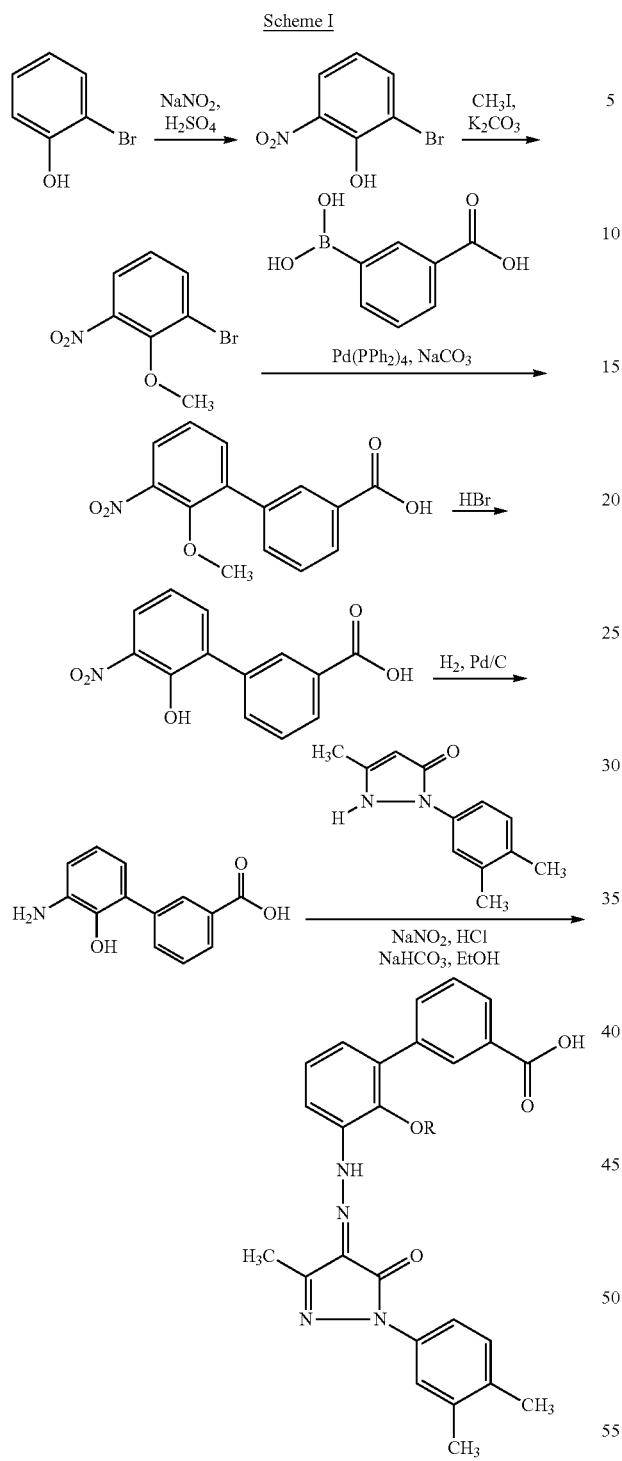

The object of the present invention is to provide a novel method, which is more convenient and more efficient than the previously known method for the synthesis of substituted 3'-hydrazino-biphenyl-3-carboxylic acid compounds.

SUMMARY OF THE INVENTION

The present invention provides a process for the preparation of substituted 3'-hydrazino-biphenyl-3-carboxylic acid compounds of formula I and salts thereof,

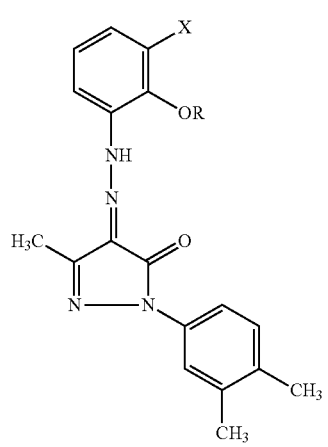

I wherein R represents hydrogen, linear or branched $C_{1-6}$ alkyl, $C_{3-8}$ cycloalkyl, optionally substituted benzyl, linear or branched alkylalkoxy, tetrahydrofuranyl, tetrahydropyranyl, methyloxybenzyl, trialkylsilyl, acyl, trityl; the process comprising:

a) reacting a compound of formula III,

III

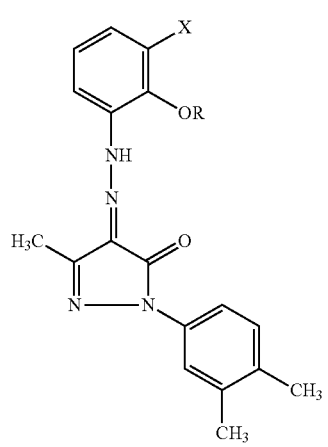

wherein R is as defined above, X is selected from the group consisting of Cl, Br, I, with a compound of formula IV.

IV

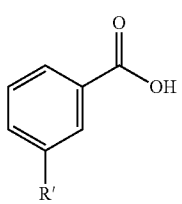

wherein R' represents boronic acid, boronic acid ester or halogen in the presence of a metal catalyst; and (b) optionally, deprotecting the compound of formula I.

In another embodiment, the present invention provides a compound of formula III,

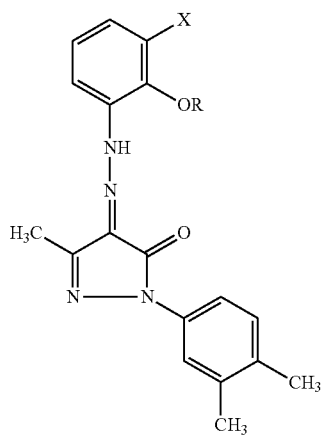

wherein X and R are as defined above.

In another embodiment, the present invention provides a compound of formula V,

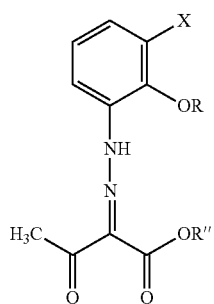

wherein X, R and R" are as defined above.

In another embodiment, the present invention provides a process for the preparation of eltrombopag, compound of formula Ia,

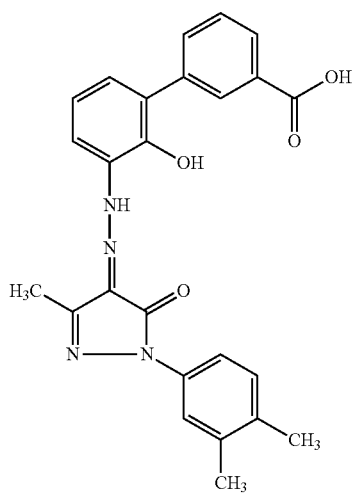

and pharmaceutically acceptable salts thereof, the process comprising:
(a) reacting 3-bromo-2-methoxyaniline with ethylacetoacetate in the presence of alkali or alkaline earth metal nitrite and inorganic acid to give ethyl 2-[(3-bromo-2-methoxyphenyl)hydrazono]-3-oxobutanoate, compound of formula Va;

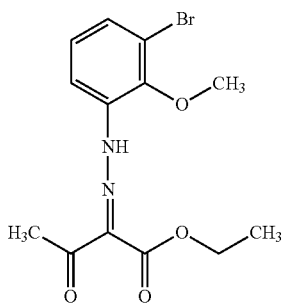

(b) reacting the compound of formula Va with 3,4-dimethylphenylhydrazine or salt thereof to give 1-(3,4-dimethylphenyl)-3-methyl-4-(3-bromo-2-methoxyphenyl)hydrazono-5-pyrazolone, compound of formula IIIa;

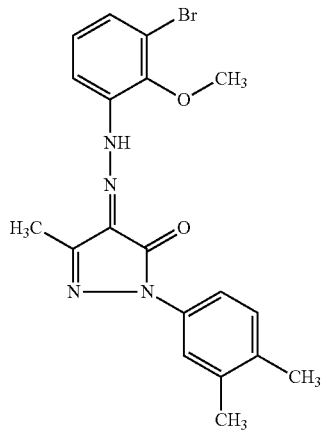

(c) reacting the compound of formula IIIa with 3-carboxyphenylboronic acid in the presence of a metal catalyst to give 3'-{N'-[1-(3,4-dimethylphenyl)-3-methyl-5-oxo-1,5-dihydro-pyrazol-4-ylidene]hydrazino}-2'-methoxybiphenyl-3-carboxylic acid, compound of formula Ib;

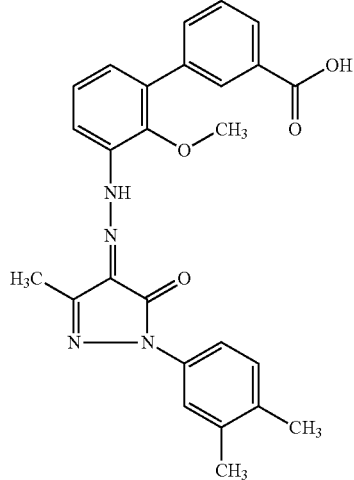

(d) deprotecting the compound of formula Ib using Lewis acid to give eltrombopag; and optionally, converting to its pharmaceutically acceptable salt.

In another embodiment, the present invention provides a process for the preparation of eltrombopag, a compound of formula Ia,

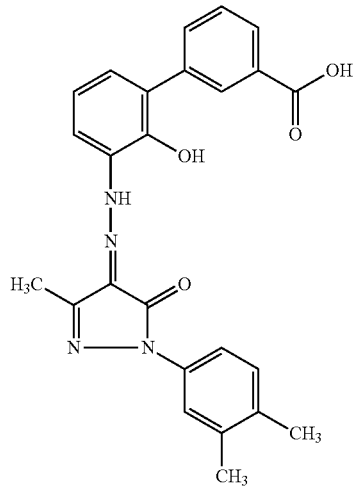

Ia the process comprising subjecting the compound of formula I to a deprotection reaction,

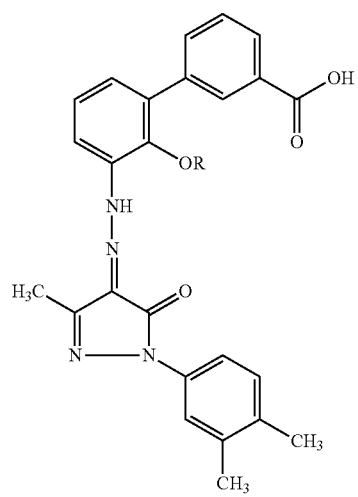

I wherein R represents linear or branched $C_{1-6}$ alkyl, $C_{3-8}$ cycloalkyl, optionally substituted benzyl, linear or branched alkylalkoxy, tetrahydrofuranyl, tetrahydropyranyl, methyloxybenzyl, trialkylsilyl, acyl, trityl.

In another embodiment, the present invention provides use of compound of formula IIIa, Va, or Ib in the preparation of eltrombopag or salt thereof.

In another embodiment, the present invention provides an eltrombopag ammonium salt.

In another embodiment, the present invention provides a process for the preparation of eltrombopag ammonium salt comprising reacting eltrombopag with a source of ammonia.

In another embodiment, the present invention provides a process for the preparation of eltrombopag olamine comprising reacting eltrombopag or a salt thereof with excess of ethanolamine without using any additional reaction solvent.

In another embodiment, the present invention provides a process for the preparation of eltrombopag olamine comprising eltrombopag or a salt thereof with ethanolamine in an aqueous medium.

In another embodiment, the present invention provides a process for the preparation of eltrombopag olamine comprising reacting eltrombopag ammonium salt with ethanolamine.

In another embodiment, the present invention provides use of eltrombopag ammonium salt in the preparation of eltrombopag olamine.

DETAILED DESCRIPTION OF THE INVENTION

Figure 1:
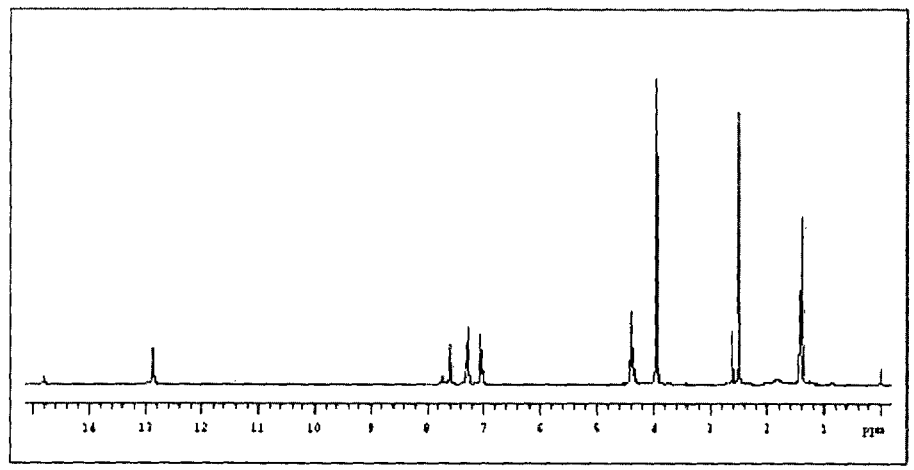
FIG. 1 is the proton NMR spectrum of ethyl 2-[(3-bromo-2-methoxyphenyl)hydrazono]-3-oxobutanoate, compound of formula Va.
Figure 2:
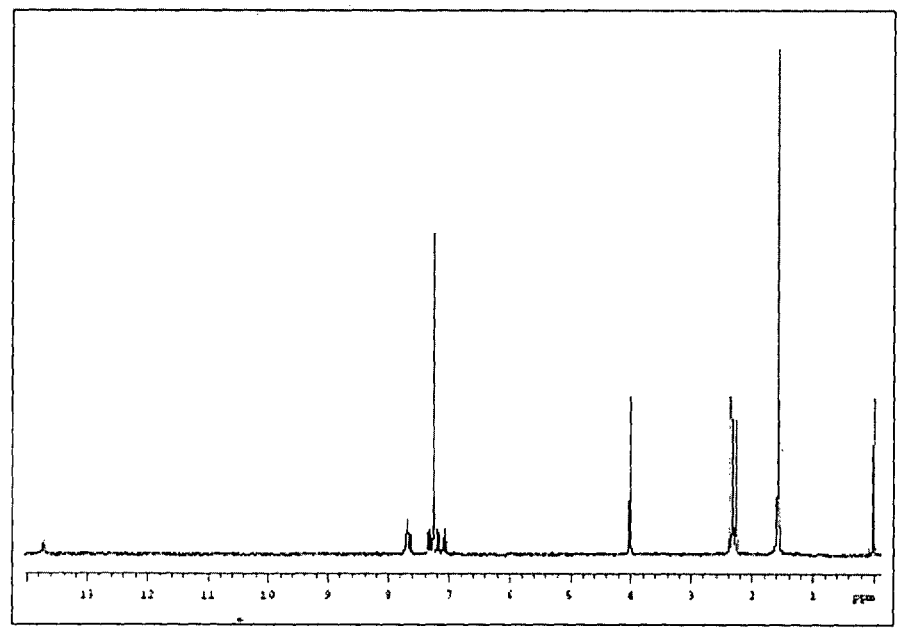
FIG. 2 is the proton NMR spectrum of 1-(3,4-dimethylphenyl)-3-methyl-4-(3-bromo-2-methoxyphenyl)hydrazono-5-pyrazolone, compound of formula IIIa.
Figure 3:
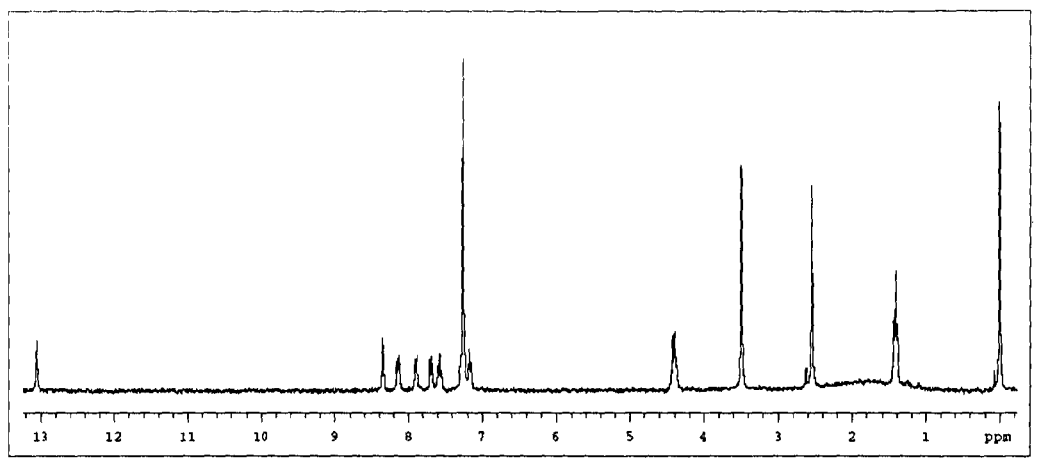
FIG. 3 is the proton NMR spectrum of 3'-{-2-[1-(ethoxycarbonyl)-2-oxopropylidene]hydrazino}-2'-methoxybiphenyl-3 -carboxylic acid.
Figure 4:
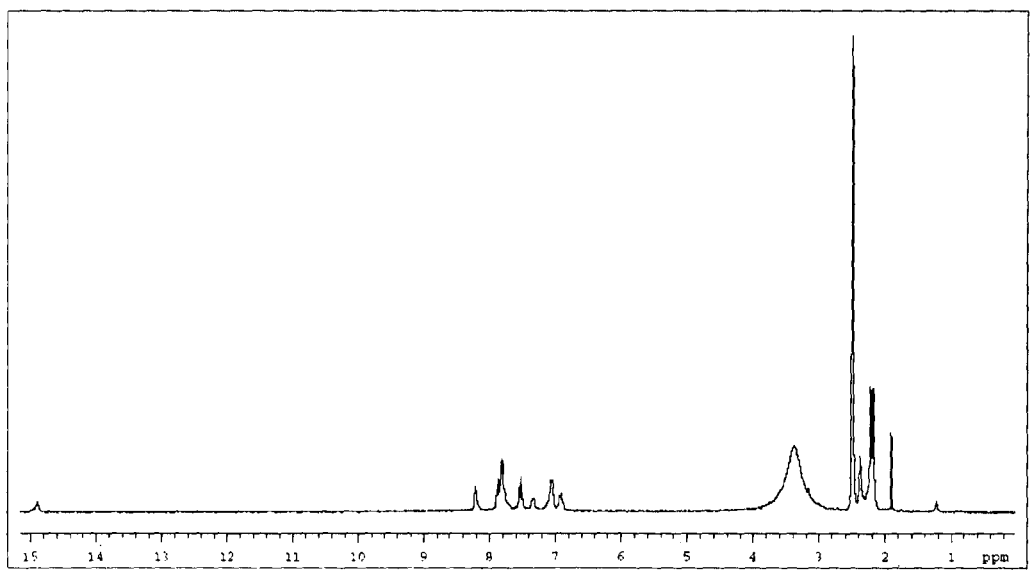
FIG. 4 is the proton NMR spectrum of eltrombopag ammonium salt as obtained in Example 14c.

The present invention provides a process for the preparation of substituted 3'-hydrazino-biphenyl-3-carboxylic acid compounds of formula I and salts thereof,

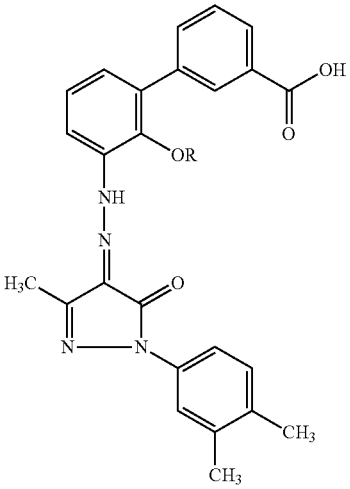

I wherein R represents hydrogen, linear or branched $C_{1-6}$ alkyl, $C_{3-8}$ cycloalkyl, optionally substituted benzyl, linear or branched alkylalkoxy, tetrahydrofuranyl, tetrahydropyranyl, methyloxybenzyl, trialkylsilyl, acyl, trityl; the process comprising:

a) reacting a compound of formula III,

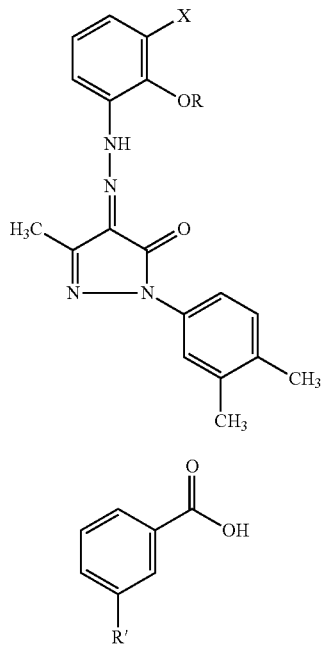

wherein R is as defined above, X is selected from the group consisting of Cl, Br, I, with a compound of formula IV, wherein R' represents boronic acid, boronic acid ester or halogen in the presence of a metal catalyst; and (b) optionally, deprotecting the compound of formula I.

In the present application, the term "room temperature" means a temperature of about 25° C. to about 30° C.

The term "linear or branched $C_{1-6}$ alkyl" includes groups such as methyl, ethyl, n-propyl, isopropyl, n-butyl, isobutyl, tert-butyl, n-pentyl. The term "$C_{3-8}$ cycloalkyl" includes groups such as cyclopropyl, cyclobutyl, cyclopentyl, cyclohexyl, cycloheptyl. The term "optionally substituted benzyl" means benzyl which is optionally substituted with halo, alkyl, alkoxy or nitro group wherein halo includes Cl, Br, I; alkyl includes methyl, ethyl, propyl, butyl; alkoxy includes methoxy, ethoxy, propoxy. The term "linear or branched alkylalkoxy" includes groups such as methylmethoxy, methylethoxy, ethylethoxy. The term "trialkylsilyl" includes groups such as trimethylsilyl, triethylsilyl, triisopropylsilyl, tert-butyldimethylsilyl. The term "acyl" includes groups such as acetyl, optionally substituted benzoyl, pivaloyl. The term "optionally substituted benzoyl" means benzoyl which is optionally substituted with halo or nitro group wherein halo includes Cl, Br, I.

In (a) of the above process, the compound of formula III, wherein X and R are as defined above is reacted with the compound of formula IV; wherein R' is as defined above, in the presence of a metal catalyst.

In one embodiment, the compound of formula III, wherein X and R are as defined above, is reacted with the compound of formula IV; wherein R' is boronic acid or boronic acid ester in the presence of a metal catalyst.

In one preferred embodiment, the compound of formula III, wherein R is $C_{1-6}$ alkyl, X is Br, is reacted with the compound of formula IV; wherein R' is boronic acid in the presence of a metal catalyst.

A suitable metal catalyst includes but is not limited to $Pd(PPh_3)_4$, $PdCl_2(PPh_3)_2$, $PdCl_2(dppf)$, $Pd(OAc)_2$, $NiCl_2(PPh_3)_2$, $PdCl_2(dppb)$. Preferably, the metal catalyst selected is $PdCl_2(PPh_3)_2$.

The reaction of compound of formula III with compound of formula IV may be carried out in the presence of base which includes organic base such as triethylamine, N-methylmorpholine, DBU; inorganic base such as lithium hydroxide, sodium hydroxide, potassium hydroxide, sodium carbonate, potassium carbonate, sodium bicarbonate, potassium bicarbonate. Preferably, the base is selected from inorganic base and more preferably the base is potassium hydroxide.

The reaction of compound of formula III with compound of formula IV may be carried out in the presence of a suitable solvent. The suitable solvent includes but is not limited to ethanol, methanol, 2-propanol, methyl acetate, ethyl acetate, acetone, ethylmethylketone, tetrahydrofuran, dioxane, toluene, dimethoxyethane, acetonitrile, dimethylformamide, dimethyl sulfoxide; water or mixtures thereof. Preferably the solvent selected is ethanol-water mixture.

The reaction of compound of formula III with compound of formula IV may be carried out at a temperature in the range of about 25° C. to about the reflux temperature of the solvent. The reaction is carried out for a period of about 3 hours to about 40 hours. Preferably the reaction is carried out at a temperature of about 70° C. to about 85° C. for a period of about 15 hour to about 30 hours.

In one embodiment, the compound of formula III, wherein X is Br and R is methyl, is reacted with the compound of formula IV; wherein R' is boronic acid, in the presence of $PdCl_2(PPh_3)_2$ catalyst and potassium hydroxide as base.

In one embodiment, the compound of formula III, wherein X and R are as defined above, is reacted with the compound of formula IV; wherein R' is halogen in the presence of a metal catalyst.

A suitable metal catalyst includes but is not limited to $Pd(PPh_3)_4$, $PdCl_2(PPh_3)_2$, $NiCl_2(PPh_3)_2$, $Ni(PPh_3)_2$. Preferably, the metal catalyst selected is $PdCl_2(PPh_3)_2$.

In one embodiment, the compound of formula III, wherein R is $C_{1-6}$ alkyl, X is Br is reacted with the compound of formula IV; wherein R' is halogen selected from the group consisting of Cl, Br, I.

In one embodiment, the compound of formula III, wherein X is Br and R is methyl, is reacted with the compound of formula IV; wherein R' is Br, in the presence of $PdCl_2(PPh_3)_2$ catalyst.

The reaction may be carried out in the presence of a suitable solvent. The suitable solvent includes but is not limited to ethanol, methanol, 1-propanol, 2-propanol, ethyl acetate, tetrahydrofuran, dioxane, acetone, toluene, dimethoxyethane, acetonitrile, dimethylformamide, dimethyl sulfoxide or mixtures thereof. Preferably the solvent selected is ethanol.

In (b) of the above process, the compound of formula I wherein R≠H, is deprotected to give eltrombopag, compound of formula Ia.

The deprotection reaction process includes any of the following:

(a) where R is $C_{1-6}$ alkyl, $C_{3-8}$ cycloalkyl, the deprotection of the compound of formula I is performed using protic acid such as hydroiodic acid, hydrobromic acid, hydrobromic acid/acetic acid, methanesulfonic acid, trifluoroacetic acid; Lewis acid selected from the group consisting of aluminium chloride, aluminium bromide, aluminium iodide, stannous chloride, stannous bromide, titanium chloride, boron trifluoride, boron tribromide, boron trifluoride-dimethylsulfide complex, beryllium chloride, beryllium bromide, zinc chloride, zinc bromide, trimethylsilylchloride, trimethylsilylbromide, trimethylsilyliodide, lithium iodide, lithium iodide in refluxing 2,4,6-collidine, pyridine hydrochloride; sulphur compounds such as sodium ethylmercaptide, sodium trimethylsilanethiolate; alkali organomides such as sodium bis(trimethylsilyl)amide and lithium diisopropylamide; or (b) where R is optionally substituted benzyl, methyloxybenzyl, the deprotection of the compound of formula I is performed via hydrogenation reaction using hydrogen in the presence of a metal catalyst; or (c) where R is linear or branched alkylalkoxy, tetrahydrofuranyl, tetrahydropyranyl, trityl, the deprotection of the compound of formula I is performed using an inorganic acid selected from the group consisting of hydrochloric acid, hydrobromic acid, sulfuric acid, phosphoric acid; organic acid such as acetic acid; or (d) where R is trialkylsilyl, the deprotection of the compound of formula I is performed using acids such as acetic acid or fluorides such as tetrabutylammonium fluoride; or (e) where R is acyl, the deprotection of the compound of formula I is performed using an inorganic acid selected from the group consisting of hydrochloric acid, hydrobromic acid, sulfuric acid, phosphoric acid; inorganic base selected from the group consisting of sodium hydroxide, potassium hydroxide, sodium carbonate, potassium carbonate.

In one embodiment, the compound of formula I wherein R is methyl is deprotected using aqueous hydrobromic acid to give eltrombopag, compound of formula Ia.

The reaction may be carried out at a temperature in the range of about 25° C. to about 125° C. The reaction is carried out for a period of about 2 hours to about 80 hours. Preferably the reaction is carried out at a temperature of about 110° C. to about 115° C. for a period of about 35 hours to about 65 hours.

In one embodiment, the compound of formula I wherein R is methyl is deprotected using Lewis acid such as aluminium chloride to give eltrombopag, compound of formula Ia.

In one embodiment, the compound of formula I wherein R is methyl is deprotected using Lewis acid such as aluminium chloride to give solid eltrombopag-aluminium complex which on acid treatment gives eltrombopag, compound of formula Ia.

The reaction may be carried out in the presence of a suitable solvent. The suitable solvent includes but is not limited to chloroform, dichloromethane, dichloroethane, toluene, xylene, chlorobenzene, tetrahydrofuran, dioxane, tert-butylmethyl ether, dimethoxyethane. Preferably the solvent selected is toluene, tetrahydrofuran.

The reaction may be carried out at a temperature in the range of about 20° C. to about 125° C. The reaction is carried out for a period of about 2 hours to about 80 hours. Preferably the reaction is carried out at a temperature of about 25° C. to about 40° C. for a period of about 35 hour to about 65 hours to give eltrombopag-aluminium complex.

The eltrombopag-aluminium complex on acid treatment gives eltrombopag, compound of formula Ia. The acid used includes hydrochloric acid, hydrobromic acid, sulfuric acid, nitric acid, phosphoric acid, acetic acid. Preferably, the acid used is acetic acid. The reaction may be carried out in the presence of a suitable solvent. The suitable solvent includes but is not limited to tetrahydrofuran, methanol, ethanol, 2-propanol. The reaction may be carried out at a temperature in the range of about 25° C. to about 125° C. The reaction is carried out for a period of about 2 hours to about 80 hours. Preferably the reaction is carried out at a temperature of about 40° C. to about 120° C. for a period of about 2 hour to about 24 hours.

In one embodiment, the present invention provides a process for the preparation of compound of formula I wherein R is H, the process comprising reacting compound of formula III wherein R is $C_{1-6}$ alkyl and X is Cl, Br, I, with compound of formula IV wherein R' is boronic acid in the presence of a metal catalyst to give compound of formula I wherein R is $C_{1-6}$ alkyl followed by deprotecting the compound of formula I wherein R is $C_{1-6}$ alkyl to give compound of formula I wherein R is H.

In one embodiment, the present invention provides a process for the preparation of compound of formula I wherein R is H, the process comprising reacting compound of formula III wherein R is methyl and X is Br, with compound of formula IV wherein R' is boronic acid in the presence of $PdCl_2(PPh_3)_2$ catalyst to give compound of formula I wherein R is methyl followed by deprotecting the compound of formula I wherein R is methyl using aqueous hydrobromic acid to give compound of formula I wherein R is H.

In one embodiment, the present invention provides a process for the preparation of compound of formula I wherein R is H, the process comprising reacting compound of formula III wherein R is methyl and X is Br, with compound of formula IV wherein R' is boronic acid in the presence of $PdCl_2(PPh_3)_2$ catalyst to give compound of formula I wherein R is methyl followed by deprotecting the compound of formula I wherein R is methyl using Lewis acid such as aluminium chloride to give compound of formula I wherein R is H.

In one embodiment, the present invention provides a process for isolating eltrombopag from an aqueous medium.

The present invention provides a compound of formula III,

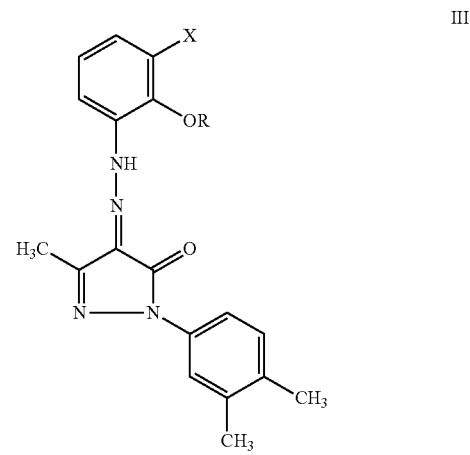

wherein X and R are as defined above.

In one embodiment, the present invention provides a compound of formula III, wherein X is Br and R is methyl.

The present invention provides a process for the preparation of compound of formula III which comprises reacting a compound of formula V,

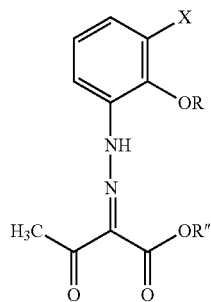

V wherein X and R are as defined above and RH represents hydrogen, $C_{1-6}$ alkyl, with 3,4-dimethylphenylhydrazine or salt thereof to give the compound of formula III.

The reaction may be carried out in the presence of alkali metal acetate such as sodium acetate, potassium acetate and the like; potassium carbonate, sodium carbonate. Preferably, alkali metal acetate is used; more preferably, sodium acetate is used.

The reaction may be carried out in the presence of a suitable solvent. The suitable solvent includes but is not limited to acetic acid, methanol, ethanol, 2-propanol or mixtures thereof. Preferably the solvent selected is acetic acid.

The reaction may be carried out at a temperature in the range of about 25° C. to about the reflux temperature of the solvent. The reaction is carried out for a period of about 1 hour to about 10 hours. Preferably the reaction is carried out at about the reflux temperature of the solvent for a period of about 2 hours to about 5 hours.

In one embodiment, the present invention provides a process for the preparation of compound of formula III, the process comprising reacting a compound of formula V with 3,4-dimethylphenylhydrazine or salt thereof to give the compound of formula III, wherein X is Br, R is methyl and R" is ethyl.

The present invention provides a compound of formula V,

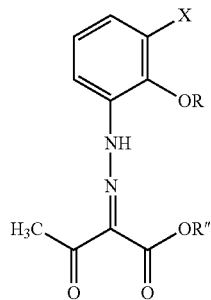

V wherein X, R and R" are as defined above.

In one embodiment, the present invention provides a compound of formula V, wherein X is Br, R is methyl and R" is ethyl.

The present invention provides a process for the preparation of compound of formula V which comprises reacting a compound of formula VI or its salt thereof,

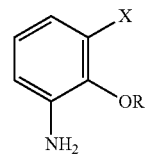

VI wherein X and R are as defined above,
with alkyl acetoacetate or acetoacetic acid in the presence of alkali or alkaline earth metal nitrite and an inorganic acid in a solvent system to yield the compound of formula V.

The reaction may be carried out in the presence of alkali metal nitrite such as sodium nitrite, potassium nitrite and the like; alkaline earth metal nitrite such as calcium nitrite and the like. Preferably, sodium nitrite is used.

The inorganic acid is selected from the group consisting of hydrochloric acid, nitric acid, sulfuric acid, hydrobromic acid. Preferably, hydrochloric acid is used.

The reaction may be carried out in the presence of a suitable solvent. The suitable solvent includes but is not limited to methanol, ethanol, 1-propanol, 2-propanol, water or mixtures thereof. Preferably the solvent selected is methanol, water, ethanol-water mixture.

The reaction may be carried out at a temperature in the range of about 0° C. to about 10° C. The reaction is carried out for a period of about 2 hours to about 8 hours. Preferably the reaction is carried out at a temperature about 0° C. to about 5° C. for a period of about 2 hours to about 6 hours.

In one embodiment, the present invention provides a process for the preparation of compound of formula V, the process comprising reacting a compound of formula VI with alkyl acetoacetate in presence of sodium nitrite and hydrochloric acid to yield the compound of formula V, wherein X is Br, R is methyl and R" is ethyl.

The present invention provides a process for the preparation of eltrombopag, compound of formula Ia,

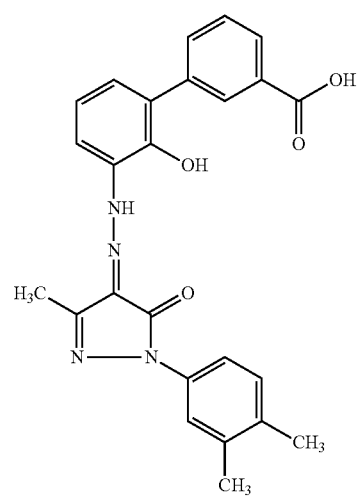

Ia and pharmaceutically acceptable salts thereof, the process comprising:
(a) reacting 3-bromo-2-methoxyaniline with ethylacetoacetate in the presence of alkali or alkaline earth metal nitrite and inorganic acid to give ethyl 2-[(3-bromo-2-methoxyphenyl)hydrazono]-3-oxobutanoate, compound of formula Va;

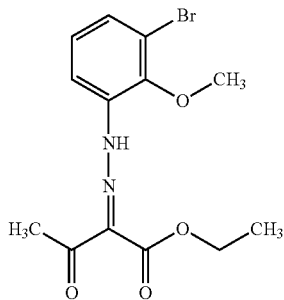

(b) reacting the compound of formula Va with 3.4-dimethylphenylhydrazine or salt thereof to give 1-(3,4-dimethylphenyl)-3-methyl-4-(3-bromo-2-methoxyphenyl)hydrazono-5-pyrazolone, compound of formula IIIa;

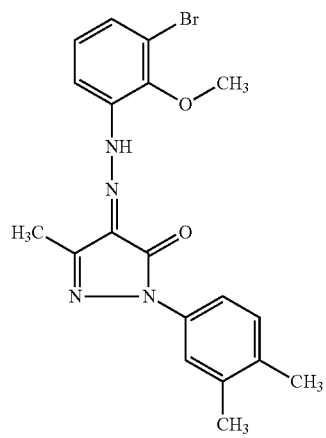

(c) reacting the compound of formula IIIa with 3-carboxyphenylboronic acid in the presence of a metal catalyst to give 3'-{N'-[1-(3,4-dimethylphenyl)-3-methyl-5-oxo-1,5-dihydro-pyrazol-4-ylidene]hydrazino}-2'-methoxybiphenyl-3-carboxylic acid, compound of formula Ib;

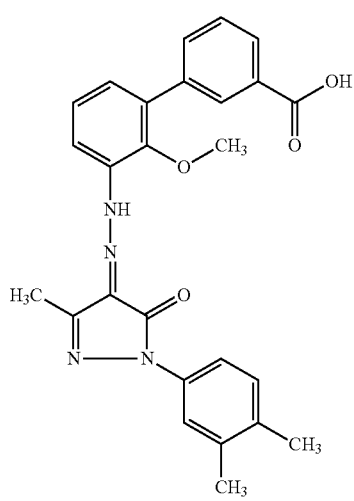

(d) deprotecting the compound of formula Ib using Lewis acid to give eltrombopag; and optionally, converting to its pharmaceutically acceptable salt.

In (a) of the above process, 3-bromo-2-methoxyaniline is reacted with ethylacetoacetate in presence of alkali or alkaline earth metal nitrite and inorganic acid to give ethyl 2-[(3-bromo-2-methoxyphenyl)hydrazono]-3-oxobutanoate, compound of formula Va.

The reaction may be carried out in the presence of alkali metal nitrite such as sodium nitrite, potassium nitrite and the like; alkaline earth metal nitrite such as calcium nitrite and the like. Preferably, sodium nitrite is used. The inorganic acid is selected from the group consisting of hydrochloric acid, nitric acid, sulfuric acid, hydrobromic acid. Preferably, hydrochloric acid is used. The reaction may be carried out in the presence of a suitable solvent. The suitable solvent includes but is not limited to methanol, ethanol, 1-propanol, 2-propanol, water or mixtures thereof. Preferably the solvent selected is methanol, water, ethanol-water mixture.

In (b) of the above process, the compound of formula Va is reacted with 3,4-dimethylphenylhydrazine or salt thereof to give 1-(3,4-dimethylphenyl)-3-methyl-4-(3-bromo-2-methoxyphenyl)hydrazono-5-pyrazolone, compound of formula IIIa.

The reaction may be carried out in the presence of alkali metal acetate such as sodium acetate, potassium acetate and the like; sodium carbonate, potassium carbonate. Preferably, the alkali metal acetate used is sodium acetate. The reaction may be carried out in the presence of a suitable solvent. The suitable solvent includes but is not limited to acetic acid, methanol, ethanol or mixtures thereof. Preferably the solvent selected is acetic acid. The reaction may be carried out at a temperature in the range of about 25° C. to about the reflux temperature of the solvent. The reaction is carried out for a period of about 1 hour to about 10 hours. Preferably the reaction is carried out at to about the reflux temperature of the solvent for a period of about 2 h to about 5 h.

In (c) of the above process, the compound of formula IIIa with 3-carboxyphenylboronic acid in presence of metal catalyst to give 3'-{N'-[1-(3,4-dimethylphenyl)-3-methyl-5-oxo-1,5-dihydro-pyrazol-4-ylidene]hydrazino}-2'-methoxybiphenyl-3-carboxylic acid, compound of formula Ib.

A suitable metal catalyst includes but is not limited to $Pd(PPh_3)_4$, $PdCl_2(PPh_3)_2$, $PdCl_2(dppf)$, $Pd(OAc)_2$, $NiCl_2(PPh_3)_2$, $PdCl_2(dppb)$. Preferably, the metal catalyst selected is $PdCl_2(PPh_3)_2$. The reaction may carried out in the presence of base which includes organic base such as triethylamine, N-methylmorpholine, DBU; inorganic base such as lithium hydroxide, sodium hydroxide, potassium hydroxide, sodium carbonate, potassium carbonate, sodium bicarbonate, potassium bicarbonate. Preferably, the base is selected from inorganic base and more preferably the base is potassium hydroxide. The reaction may carried out in the presence of a suitable solvent. The suitable solvent includes but is not limited to ethanol, methanol, 2-propanol, methyl acetate, ethyl acetate, acetone, ethylmethylketone, tetrahydrofuran, dioxane, toluene, dimethoxyethane, acetonitrile, dimethylformamide; water or mixtures thereof. Preferably the solvent selected is ethanol-water mixture. The reaction may be carried out at a temperature in the range of about 25° C. to about the reflux temperature of the solvent. The reaction is carried out for a period of about 3 hours to about 40 hours. Preferably the reaction is-carried out at a temperature of about 70° C. to about 85° C. for a period of about 15 hours to about 30 hours.

In (d) of the above process, the compound of formula Ib is deprotected using Lewis acid to give eltrombopag.

In one embodiment, the compound of formula Ib is deprotected using Lewis acid selected from the group consisting of aluminium chloride, aluminium bromide, aluminium iodide, stannous chloride, stannous bromide, titanium chloride, boron trifluoride, boron tribromide, boron trifluoride-dimethylsulfide complex, beryllium chloride, beryllium bromide, zinc chloride, zinc bromide, trimethylsilylchloride, trimethylsilylbromide, trimethylsilyliodide.

In one embodiment, the compound of formula Ib is deprotected using Lewis acid such as aluminium chloride to give solid eltrombopag-aluminium complex which on acid treatment gives eltrombopag. The deprotection reaction process is as discussed supra.

The present invention provides a process for the preparation of eltrombopag, a compound of formula Ia,

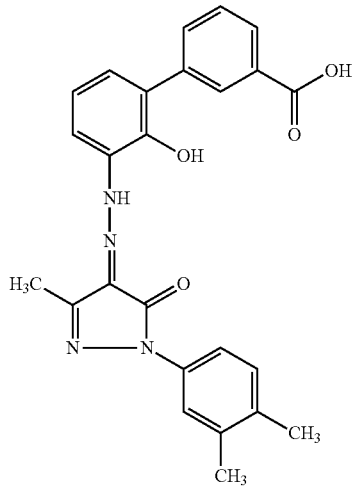

Ia the process comprising subjecting the compound of formula I to a deprotection reaction,

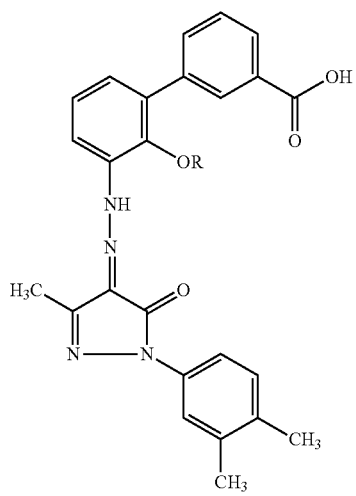

I wherein R represents linear or branched $C_{1-6}$ alkyl, $C_{3-8}$ cycloalkyl, optionally substituted benzyl, linear or branched alkylalkoxy, tetrahydrofuranyl, tetrahydropyranyl, methyloxybenzyl, trialkylsilyl, acyl, trityl.

In one embodiment, the present invention provides a process for the preparation of eltrombopag comprising subjecting the compound of formula I wherein R is $C_{1-6}$ alkyl, $C_{3-8}$ cycloalkyl, to a deprotection reaction using protic acid such as hydroiodic acid, hydrobromic acid, hydrobromic acid/acetic acid, methanesulfonic acid, trifluoroacetic acid; Lewis acid selected from the group consisting of aluminium chloride, aluminium bromide, aluminium iodide, stannous chloride, stannous bromide, titanium chloride, boron trifluoride, boron tribromide, boron trifluoride-dimethylsulfide complex, beryllium chloride, beryllium bromide, zinc chloride, zinc bromide, trimethylsilylchloride, trimethylsilylbromide, trimethylsilyliodide, lithium iodide, lithium iodide in refluxing 2,4,6-collidine, pyridine hydrochloride; sulphur compounds such as sodium ethylmercaptide, sodium trimethylsilanethiolate; alkali organomides such as sodium bis(trimethylsilyl)amide and lithium diisopropylamide.

In one embodiment, the present invention provides a process for the preparation of eltrombopag, the process comprising subjecting the compound of formula I wherein where R is optionally substituted benzyl, methyloxybenzyl, to a deprotection reaction by hydrogenation using hydrogen in the presence of a metal catalyst.

In one embodiment, the present invention provides a process for the preparation of eltrombopag, the process comprising subjecting the compound of formula I wherein R is linear or branched alkylalkoxy, tetrahydrofuranyl, tetrahydropyranyl, trityl, to a deprotection reaction using an inorganic acid selected from the group consisting of hydrochloric acid, hydrobromic acid, sulfuric acid, phosphoric acid; organic acid such as acetic acid.

In one embodiment, the present invention provides a process for the preparation of eltrombopag, the process comprising subjecting the compound of formula I wherein R is trialkylsilyl, to a deprotection reaction using acids such as acetic acid or fluorides such as tetrabutylammonium fluoride.

In one embodiment, the present invention provides a process for the preparation of eltrombopag, the process comprising subjecting the compound of formula I wherein R is acyl, to a deprotection reaction using an inorganic acid selected from the group consisting of hydrochloric acid, hydrobromic acid, sulfuric acid, phosphoric acid; inorganic base selected from the group consisting of sodium hydroxide, potassium hydroxide, sodium carbonate, potassium carbonate.

In one embodiment, the present invention provides a process for the preparation of eltrombopag, the process comprising subjecting the compound of formula I wherein R is methyl, to a deprotection reaction using hydrobromic acid.

In one embodiment, the present invention provides a process for the preparation of eltrombopag, the process comprising subjecting the compound of formula I wherein R is methyl, to a deprotection reaction using Lewis acid.

In one embodiment, the present invention provides a process for the preparation of eltrombopag, compound of formula Ia, the process comprising deprotecting the compound of formula I wherein R is methyl, using a Lewis acid such as aluminium chloride to give solid eltrombopag-aluminium complex, then on acid treatment gives eltrombopag, compound of formula Ia.

The reaction may be carried out in the presence of a suitable solvent. The suitable solvent includes but is not limited to chloroform, dichloromethane, dichloroethane, toluene, xylene, chlorobenzene, tetrahydrofuran, dioxane, tert-butylmethyl ether, dimethoxyethane. Preferably the solvent selected is toluene, tetrahydrofuran.

The reaction may be carried out at a temperature in the range of about 20° C. to about 125° C. The reaction is carried out for a period of about 2 hours to about 80 hours. Preferably the reaction is carried out at a temperature of about 25° C. to about 40° C. for a period of about 35 hours to about 65 hours to give eltrombopag-aluminium complex.

The eltrombopag-aluminium complex on acid treatment gives eltrombopag, compound of formula Ia. The acid used includes hydrochloric acid, hydrobromic acid, sulfuric acid, nitric acid, phosphoric acid, acetic acid. Preferably, the acid used is acetic acid. The suitable solvent includes but is not limited to tetrahydrofuran, methanol, ethanol, 2-propanol. The reaction may be carried out at a temperature in the range of about 25° C. to about 125° C. The reaction is carried out for a period of about 2 hours to about 80 hours. Preferably the reaction is carried out at a temperature of about 40° C. to about 120° C. for a period of about 2 hour to about 24 hours.

The present invention provides an eltrombopag-aluminium complex.

The present invention provides a solid eltrombopag-aluminium complex.

The present invention provides use of compound of formula III, or V in the preparation of eltrombopag or salt thereof.

The present invention provides use of compound of, formula I, wherein R represents linear or branched $C_{1-6}$ alkyl, $C_{3-8}$ cycloalkyl, optionally substituted benzyl, linear or branched alkylalkoxy, tetrahydrofuranyl, tetrahydropyranyl, methyloxybenzyl, trialkylsilyl, acyl, trityl in the preparation of eltrombopag or salt thereof.

In one embodiment, the present invention provides use of compound of formula IIIa, Va, or Ib in the preparation of eltrombopag and salt thereof.

The present invention provides a process for the preparation of substituted 3'-hydrazino-biphenyl-3-carboxylic acid compounds of formula I and salts thereof,

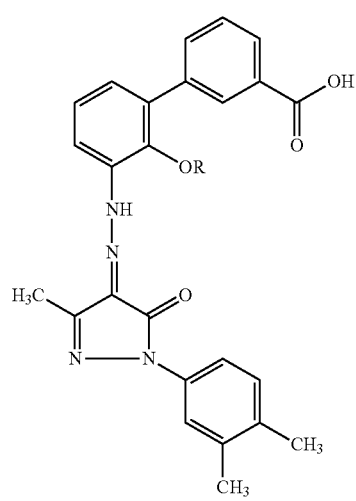

I wherein R represents hydrogen, linear or branched $C_{1-6}$ alkyl, $C_{3-8}$ cycloalkyl, optionally substituted benzyl, linear or branched alkylalkoxy, tetrahydrofuranyl, tetrahydropyranyl, methyloxybenzyl, trialkylsilyl, acyl, trityl; the process comprising:

a) reacting a compound of formula VII,

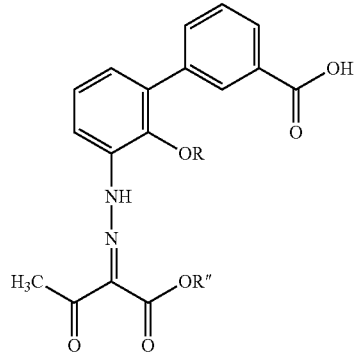

VII wherein R is as defined above and R" represents hydrogen, $C_{1-6}$ alkyl, with 3,4-dimethylphenylhydrazine or salt thereof to give the compound of formula I; and b) optionally, deprotecting the compound of formula I.

In (a) of the above process, the reaction may be carried out in the presence of alkali metal acetate such as sodium acetate, potassium acetate and the like; potassium carbonate, sodium carbonate. Preferably, alkali metal acetate is used: more preferably, sodium acetate is used. The reaction may be carried out in the presence of a suitable solvent. The suitable solvent includes but is not limited to acetic acid, methanol, ethanol, 2-propanol or mixtures thereof. Preferably the solvent selected is acetic acid. The reaction may be carried out at a temperature in the range of about 25° C. to about the reflux temperature of the solvent. The reaction is carried out for a period of about 1 hour to about 10 hours. Preferably the reaction is carried out at about the reflux temperature of the solvent for a period of about 2 h to abdut 5 h.

In one embodiment, the compound of formula VII is reacted with 3,4-dimethylphenylhydrazine or salt thereof to give the compound of formula I, wherein R is methyl and R" is ethyl.

In (b) of the above process, the compound of formula I wherein R≠H, is deprotected to give eltrombopag, compound of formula Ia. The deprotection reaction process is as discussed supra.

In one embodiment, the present invention provides a process for the preparation of compound of formula I wherein R is H, the process comprising reacting compound of formula VII wherein R is $C_{1-6}$ alkyl and R" is hydrogen, $C_{1-6}$ alkyl with 3,4-dimethylphenylhydrazine or salt thereof to give the compound of formula I wherein R is $C_{1-6}$ alkyl followed by deprotecting the compound of formula I wherein R is $C_{1-6}$ alkyl using aqueous hydrobromic acid, Lewis acid such as aluminium chloride to give compound of formula I wherein R is H.

The present invention provides a compound of formula VII,

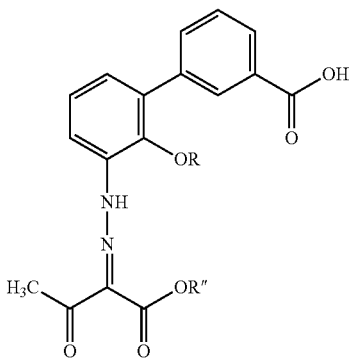

VII wherein R represents hydrogen, linear or branched $C_{1-6}$ alkyl, $C_{3-8}$ cycloalkyl, optionally substituted benzyl, linear or branched alkylalkoxy, tetrahydrofuranyl, tetrahydropyranyl, methyloxybenzyl, trialkylsilyl, acyl, trityl; and R" represents hydrogen, $C_{1-6}$ alkyl.

In one embodiment, the present invention provides a compound of formula V, wherein R is methyl and R" is ethyl.

The present invention provides a process for the preparation of compound of formula VII, the process comprising:
a) reacting a compound of formula VI, wherein X and R are as defined above, with a compound of formula IV, wherein R' is as defined above,

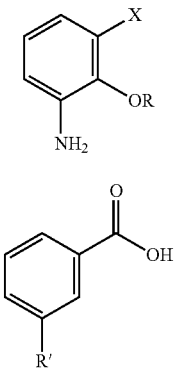

VI

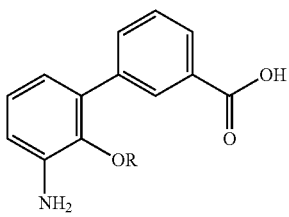

IV in the presence of a metal catalyst to give a compound of formula VIII,

VIII wherein R is as defined above; and
b) reacting the compound of formula VIII with alkyl acetoacetate or acetoacetic acid in the presence of alkali or alkaline earth metal nitrite and an inorganic acid to yield the compound of formula VII.

In (a) of the above process, the compound of formula VI, wherein X and R are as defined above, is reacted with the compound of formula IV; wherein R' is boronic acid or boronic acid ester or halogen in the presence of a metal catalyst to give the compound of formula VIII, wherein R is as defined above.

A suitable metal catalyst includes but is not limited to $Pd(PPh_3)_4$, $PdCl_2(PPh_3)_2$, $PdCl_2(dppf)$, $Pd(OAc)_2$, $NiCl_2(PPh_3)_2$, $PdCl_2(dppb)$. Preferably, the metal catalyst selected is $PdCl_2(PPh_3)_2$. The reaction of compound of formula VI with compound of formula IV may be carried out in the presence of base which includes organic base such as triethylamine, N-methylmorpholine, DBU; inorganic base such as lithium hydroxide, sodium hydroxide, potassium hydroxide, sodium carbonate, potassium carbonate, sodium bicarbonate, potassium bicarbonate. Preferably, the base is selected from inorganic base and more preferably the base is potassium hydroxide, potassium carbonate. The reaction of compound of formula VI with compound of formula IV may be carried out in the presence of a suitable solvent. The suitable solvent includes but is not limited to ethanol, methanol, 2-propanol, methyl acetate, ethyl acetate, acetone, ethylmethylketone, tetrahydrofuran, dioxane, toluene, dimethoxyethane, acetonitrile, dimethylformamide, dimethyl sulfoxide; water or mixtures thereof. Preferably the solvent selected is ethanol-water mixture. The reaction of compound of formula VI with compound of formula IV may be carried out at a temperature in the range of about 25° C. to about the reflux temperature of the solvent. The reaction is carried out for a period of about 3 hours to about 40 hours. Preferably the reaction is carried out at a temperature of about 70° C. to about 85° C. for a period of about 15 hour to about 30 hours.

In one embodiment, the compound of formula VI, wherein R is $C_{1-6}$ alkyl, X is Br, is reacted with the compound of formula IV; wherein R' is boronic acid in the presence of a metal catalyst.

In one embodiment, the compound of formula VI, wherein X is Br and R is methyl, is reacted with the compound of formula IV; wherein R' is boronic acid, in the presence of $PdCl_2(PPh_3)_2$ catalyst and potassium carbonate as base.

In one embodiment, the compound of formula VI, wherein R is $C_{1-6}$ alkyl, X is Br is reacted with the compound of formula IV; wherein R' is halogen selected from the group consisting of Cl, Br, I.

In (b) of the above process, the reaction may be carried out in the presence of alkali metal nitrite such as sodium nitrite, potassium nitrite and the like; alkaline earth metal nitrite such as calcium nitrite and the like. Preferably, sodium nitrite is used. The inorganic acid is selected from the group consisting of hydrochloric acid, nitric acid, sulfuric acid, hydrobromic acid. Preferably, hydrochloric acid is used. The reaction may be carried out in the presence of a suitable solvent. The suitable solvent includes but is not limited to methanol, ethanol, 1-propanol, 2-propanol, water or mixtures thereof. Preferably the solvent selected is methanol-water mixture.

In one embodiment, the compound of formula VIII, wherein R is $C_{1-6}$ alkyl, is reacted with alkyl acetoacetate or acetoacetic acid in presence of sodium nitrite and hydrochloric acid to yield the compound of formula VII, wherein R is $C_{1-6}$ alkyl and R" is hydrogen, $C_{1-6}$ alkyl.

The present invention provides a process for the preparation of compound of formula VII which comprises reacting a compound of formula V,

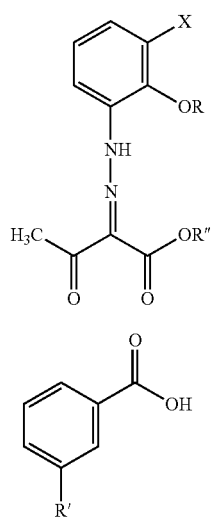

V

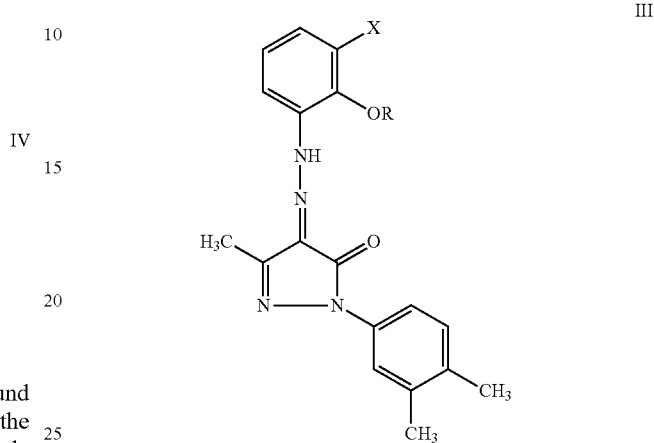

IV wherein X, R and R" are as defined above, with a compound of formula IV, wherein R' is as defined above, in the presence of a metal catalyst to give the compound of formula VII.

In one embodiment, the compound of formula V, wherein X and R are as defined above, is reacted with the compound of formula IV; wherein R' is boronic acid or boronic acid ester or halogen in the presence of a metal catalyst.

A suitable metal catalyst includes but is not limited to $Pd(PPh_3)_4$, $PdCl_2(PPh_3)_2$, $PdCl_2(dppf)$, $Pd(OAc)_2$, $NiCl_2(PPh_3)_2$, $PdCl_2(dppb)$. Preferably, the metal catalyst selected is $PdCl_2(PPh_3)_2$. The reaction of compound of formula V with compound of formula IV may be carried out in the presence of base which includes organic base such as triethylamine, N-methylmorpholine, DBU; inorganic base such as lithium hydroxide, sodium hydroxide, potassium hydroxide, sodium carbonate, potassium carbonate, sodium bicarbonate, potassium bicarbonate. Preferably, the base is selected from inorganic base and more preferably the base is potassium hydroxide, potassium carbonate. The reaction of compound of formula V with compound of formula IV may be carried out in the presence of a suitable solvent. The suitable solvent includes but is not limited to ethanol, methanol, 2-propanol, methyl acetate, ethyl acetate, acetone, ethylmethylketone, tetrahydrofuran, dioxane, toluene, dimethoxyethane, acetonitrile, dimethylformamide, dimethyl sulfoxide; water or mixtures thereof. Preferably the solvent selected is ethanol-water mixture. The reaction of compound of formula V with compound of formula IV may be carried out at a temperature in the range of about 25° C. to about the reflux temperature of the solvent. The reaction is carried out for a period of about 3 hours to about 40 hours. Preferably the reaction is carried out at a temperature of about 70° C. to about 85° C. for a period of about 15 hour to about 30 hours.

In one embodiment, the compound of formula V, wherein R is $C_{1-6}$ alkyl, X is Br, is reacted with the compound of formula IV; wherein R' is boronic acid in the presence of a metal catalyst.

In one embodiment, the compound of formula V, wherein X is Br and R is methyl, is reacted with the compound of formula IV; wherein R' is boronic acid, in the presence of $PdCl_2(PPh_3)_2$ catalyst and potassium carbonate as base.

In one embodiment, the compound of formula V, wherein R is $C_{1-6}$ alkyl, X is Br is reacted with the compound of formula IV; wherein R' is halogen selected from the group consisting of Cl, Br, I.

The present invention provides a process for the deprotection of a compound of formula III,

III wherein R represents linear or branched $C_{1-6}$ alkyl, $C_{3-8}$ cycloalkyl, optionally substituted benzyl, linear or branched alkylalkoxy, tetrahydrofuranyl, tetrahydropyranyl, methyloxybenzyl, trialkylsilyl, acyl, trityl, and X is selected from the group consisting of Cl, Br, I.

The deprotection of compound of formula III may be carried out as described for compound of formula I wherein R≠H, as discussed supra.

In one embodiment, the present invention provides a process for the deprotection of the compound of formula III, the process comprising subjecting the compound of formula III wherein R is methyl, to a deprotection reaction using hydrobromic acid, Lewis acid such as aluminium chloride.

The present invention provides an eltrombopag ammonium salt.

The present invention provides an eltrombopag ammonium salt characterized by a proton NMR spectrum having peaks at δ 14.81 (brs, 1H), 8.17 (s, 1H), 7.80-7.82(m, 3H), 7.65-7.68 (d, 1H), 7.34-7.42 (m, 2H), 7.01-7.07 (m, 2H), 6.87 (t, 1H), 2.37 (s, 3H), 2.22 (s, 3H), 2.18 (s, 3H).

The present invention provides an eltrombopag ammonium salt with ammonia content in the range of about 3.5% to about 8.5%.

The present invention provides an eltrombopag ammonium salt which may be mono-ammonium salt or di-ammonium salt, preferably in crystalline form or amorphous form.

The present invention provides a process for the preparation of eltrombopag ammonium salt comprising reacting eltrombopag with a source of ammonia.

A suitable source of ammonia includes but is not limited to ammonia water (aqueous ammonia), ammonium carbonate, ammonia gas, liquid ammonia. Preferably, the source of ammonia selected is ammonia water.

The reaction may be carried out in the presence of a suitable solvent. The suitable solvent includes but is not limited to methanol, ethanol, 1-propanol, 2-propanol, 1-butanol, 2-butanol, methyl acetate, ethyl acetate, n-propyl acetate, tert-butyl acetate, acetone, ethylmethylketone, methyl isobutyl ketone, chloroform, dichloromethane, dichloroethane, tetrahydrofuran, dioxane, tert-butylmethyl ether, toluene, xylene, chlorobenzene, dimethoxyethane, acetonitrile, dimethylformamide; water or mixtures thereof. Preferably the solvent selected is tetrahydrofuran.

The reaction may be carried out at a temperature in the range of about 10° C. to about 40° C. The reaction is carried out for a period of about 1 hour to about 20 hours. Preferably the reaction is carried out at a temperature of about 20° C. to about 35° C. for a period of about 1 hour to about 5 hours.

In one embodiment, the present invention provides a process for isolating eltrombopag as an eltrombopag ammonium salt.

Eltrombopag may be converted to its pharmaceutically acceptable salts such as its monoethanolamine, bisethanolamine salts. Preferably, eltrombopag is converted to its bisethanolamine salt namely, eltrombopag olamine; compound of formula II.

In one embodiment, the present invention provides a process for the preparation of eltrombopag olamine comprising reacting eltrombopag or a salt thereof with excess of ethanolamine without using any additional reaction solvent.

In one embodiment, the present invention provides a process for the preparation of eltrombopag olamine comprising reacting eltrombopag or a salt thereof with ethanolamine in an aqueous medium.

In one embodiment, the present invention provides a process for the preparation of eltrombopag olamine comprising reacting eltrombopag or a salt thereof with ethanolamine in water.

In one embodiment, the present invention provides a process for the preparation of eltrombopag olamine comprising reacting eltrombopag or a salt thereof with ethanolamine in a solvent and isolating eltrombopag olamine by addition of anti-solvent.

The solvent that may be utilized for this step includes, but is not limited to alcohols such as methanol, ethanol, 1-propanol, 2-propanol, 1-butanol, 2-butanol, 1-pentanol, 1-octanol and the like; ethers such as tert-butylmethyl ether, tetrahydrofuran, dioxane and the like; esters such as methyl acetate, ethyl acetate, n-propyl acetate, and tert-butyl acetate and the like; ketones such as acetone, ethyl methyl ketone and methyl isobutyl ketone and the like; dimethyl sulfoxide; dimethyl formamide; dimethyl acetamide; water and mixtures thereof.

The anti-solvent that may be utilized for this step includes, but is not limited to ethers such as diethyl ether, dimethyl ether, diisopropyl ether, tetrahydrofuran, dioxane; hydrocarbons such as n-hexane, n-heptane, cyclohexane; water and mixtures thereof: preferably non-polar anti-solvent is used.

The present invention provides a process for the preparation of eltrombopag olamine comprising reacting eltrombopag ammonium salt with ethanolamine.

In one embodiment, the present invention provides a process for the preparation of eltrombopag olamine comprising reacting eltrombopag ammonium salt with ethanolamine, preferably, without using any additional reaction solvent.

In one embodiment, the present invention provides a process for the preparation of eltrombopag olamine comprising reacting eltrombopag ammonium salt with ethanolamine in the presence of a solvent.

The solvent that may be utilized for this step includes, but is not limited to methanol, ethanol, 1-propanol, 2-propanol, 1-butanol, 2-butanol, methyl acetate, ethyl acetate, n-propyl acetate, tert-butyl acetate, acetone, ethylmethylketone, methyl isobutyl ketone, tetrahydrofuran, dioxane, tert-butylmethyl ether, toluene, dimethoxyethane, acetonitrile, dimethylformamide; water or mixtures thereof.

The present invention provides use of eltrombopag ammonium salt in the preparation of eltrombopag olamine.

In one embodiment, the present invention provides a process for the preparation of eltrombopag olamine, the process comprising: (a) treating a reaction mixture containing eltrombopag with a base to give eltrombopag salt, and (b) reacting the eltrombopag salt with ethanolamine to give eltrombopag olamine directly, wherein eltrombopag is formed in-situ in the reaction. The eltrombopag salt obtained in this step includes, but is not limited to eltrombopag sodium salt, eltrombopag potassium salt, eltrombopag ammonium salt.

In one preferred embodiment, the present invention provides a process for the preparation of eltrombopag olamine, the process comprising: (a) treating a reaction mixture containing eltrombopag with a source of ammonia to give eltrombopag ammonium salt, and (b) reacting the eltrombopag ammonium salt with ethanolamine to give eltrombopag olamine directly, wherein eltrombopag is formed in-situ in the reaction.

The present invention provides eltrombopag and a salt thereof, having a compound of formula IIIa in less than about 0.5%, preferably less than about 0.15%, more preferably less than about 0.05%.

The present invention provides eltrombopag and a salt thereof, having a compound of formula IIIb in less than about 0.5%, preferably less than about 0.15%, more preferably less than about 0.05%.

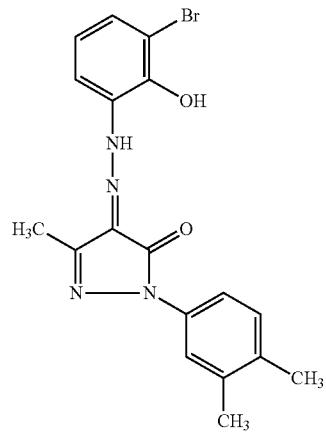

IIIb

The present invention provides eltrombopag and a salt thereof, having a compound of formula IXa in less than about 0.5%, preferably less than about 0.15%, more preferably less than about 0.05%.

27

IXa

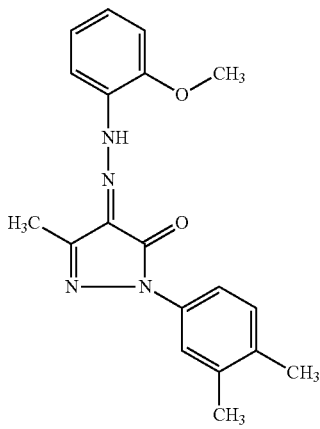

The present invention provides eltrombopag and a salt thereof, having a compound of formula IXb in less than about 0.5%, preferably less than about 0.15%, more preferably less than about 0.05%.

IXb

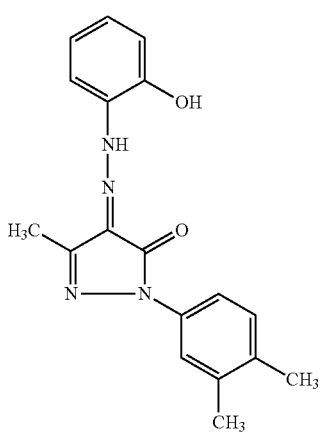

The present invention provides substituted 3'-hydrazinobiphenyl-3-carboxylic acid compounds of formula I, salts thereof and intermediate compounds, obtained by the above processes, as characterized and analyzed by following techniques:

A: Proton NMR spectra were recorded in CDCl$_3$ and DMSO-d$_6$ using NMR instrument—Varian 300 MHZ B. IR spectra were recorded using IR instrument—Perkin Elmer Spectrum One FTIR and all the samples prepared in KBr.

C. Mass spectra were recorded using instrument—Thermofinnigan, LCQ DECA XP MAX

D. HPLC

F. Melting point

The following examples are provided to enable one skilled in the art to practice the invention and are merely illustrative of the invention. The examples should not be read as limiting the scope of the invention as defined in the features and advantages.

28

EXAMPLES

Example 1

Preparation of Ethyl 2-[(3-bromo-2-methoxyphenyl) hydrazono]-3-oxobutanoate

To a solution of 3-bromo-2-methoxyaniline (20 g) in 1N hydrochloric acid (400 mL) was added a solution of sodium nitrite (7.2 g in 720 mL of water) at about 0° C. to about 5° C. under stirring. The reaction mixture was stirred for about 15 minutes at about 5° C. Then ethyladetoacetate (12.9 g) was added to the reaction mixture and stirred for about 15 minutes at about 0° C. to about 5° C. Sodium bicarbonate solution (27.5 g in 300 mL water) and ethanol (400 mL) was then added to the reaction mixture. The reaction mixture was allowed to warm to about room temperature and stirred for about 2 hours. The mixture was filtered, washed with water (200 mL) and dried to get yellowish solid. Yield: 33 g; Melting point: 75.9-77.1° C.; Purity (HPLC): 99.12%

IR: 3421, 1706, 1684, 1517, 1215, 1093, 980 cm$^{-1}$; Mass: m/z 342.88 [M+] and 344.86 [M+2]

$^1$H NMR (300 MHz in CDCl$_3$): δ 12.86 (s, 1H), 7.58-7.61 (d, 1H), 7.30-7.33 (d, 1H), 7.02-7.07 (m, 1H), 4.31-4.43 (q, 2H), 3.95 (s, 3H), 2.5 (s, 3H), 1.38-1.43 (t, 3H)

Example 2

Preparation of 1-(3,4-dimethylphenyl)-3-methyl-4-(3-bromo-2-methoxyphenyl)hydrazono-5-pyrazolone A solution of ethyl-2-[(3-bromo-2-methoxyphenyl)hydrazono]-3-oxobutanoate (5 g) prepared as in Example 1, and 3,4-dimethylphenylhydrazine hydrochloride (2.48 g) and sodium acetate (1.4 g) in glacial acetic acid (100 mL) was stirred and heated to reflux for about 3 hours. The mixture was cooled to about room temperature and stirred for about 1 hour. It was filtered, washed with water (25 mL) and dried in an oven at about 55° C. to about 60° C. for about 12 hours to obtain an orange solid product. Yield: 4.15 g; Melting point: 197.4-198.2° C.; Purity (HPLC): 99.33%

IR: 3444, 1559, 1337, 1256, 1114, 1019 cm$^{-1}$; Mass: m/z 415 [M+] and 417 [M+2]

$^1$H NMR (300 MHz in CDCl$_3$): δ 13.7 (brs, 1H), 7.64-7.73 (m, 3H), 7.32-7.35 (d, 1H), 7.16-7.19 (d, 1H), 7.07-7.16 (t, 1H), 4.01 (s, 3H), 2.36 (s, 3H), 2.31 (s, 3H), 2.27 (s, 3H)

Example 3

Preparation of 3'-{N'-[1-(3,4-dimethylphenyl)-3-methyl-5-oxo-1,5-dihydro-pyrazol-4-ylidene]hydrazino}-2'-methoxybiphenyl-3-carboxylic acid A mixture of 1-(3,4-dimethylphenyl)-3-methyl-4-(3-bromo-2-methoxyphenyl)hydrazono-5-pyrazolone (5 g) prepared as in Example 2, and 3-carboxyphenylboronic acid (2.99 g), bis(triphenylphosphine)palladium(II)chloride [PdCl$_2$(PPh$_3$)$_2$] (0.42 g), potassium hydroxide (1.74 g) in ethanol. (250 mL) and water (30 mL) was heated to about reflux temperature and stirred for about 24 hours. The hot mixture was filtered to remove the catalyst. The clear filtrate was concentrated under vacuum. To the residue, water (100 mL) was added; acidified to pH 3-5 using hydrochloric acid and stirred for about 30 minutes at about room temperature. The slurry was filtered to give a yellowish orange solid product, which was washed with water (50 mL) and dried in an oven at about 55° C. to about 60° C. for about 12 hours.

Yield: 4 g; Melting point: 256.5-257.2° C.; Mass: m/z 455.61 [M−1]

IR: 3413, 1687, 1546, 1501, 1258, 1003 cm$^{-1}$ $^1$H NMR (300 MHz in DMSO-d$_6$): δ 13.7 (brs, 1H), 13 (brs, 1H), 8.17 (s, 1H), 7.98-8.01 (d, 1H), 7.87-7.96 (d, 1H), 7.78-7.84 (d, 1H), 7.58-7.75 (m, 3H), 7.36-7.52 (m, 1H), 7.29-7.34 (d, 1H), 7.18-7.26 (d, 1H), 3.44 (s, 3H), 2.32 (s, 3H), 2.25 (s, 3H), 2.21 (s, 3H)

Example 4

Preparation of 3'-{N'-[1-(3,4-dimethylphenyl)-3-methyl-5-oxo-1,5-dihydro-pyrazol-4-ylidene]hydrazino}-2'-hydroxybiphenyl-3-carboxylic acid A solution of 3'-{N'-[1-(3,4-dimethylphenyl)-3-methyl-5-oxo-1,5-dihydro-pyrazol-4-ylidene]hydrazino}-2'-methoxybiphenyl-3-carboxylic acid (4 g), prepared as in Example 3, in 48% aqueous hydrobromic acid (35 mL) and glacial acetic acid (35 mL) was stirred and heated under reflux for about 60 hours. The reaction mixture was concentrated under vacuum to a thick residue. Water (40 mL) was added and basified to pH 7-8 using saturated solution of sodium bicarbonate (20 mL). The mixture was filtered to give an orange solid, which was washed with water (25 mL) and dried in an oven at 55° C. about to about 60° C. for about 12 hours.

Yield: 3 g; Melting point: 231.6-232.9° C.; Mass: m/z 443.16 [M+1]

IR: 3292, 1707, 1541, 1503, 1223, 1118, 1000 cm$^{-1}$ $^1$H NMR (300 MHz in DMSO-d$_6$): δ 13.75 (brs, 1H), 13.09 (brs, 1H), 9.69 (s, 1H), 8.13 (s, 1H), 7.94-7.97 (d, 1H), 7.79-7.82 (d, 1H), 7.62-7.71 (m, 3H), 7.16-7.21 (m, 3H), 2.32 (s, 3H), 2.26 (s, 3H), 2.22 (s, 3H)

Example 5

Preparation of Eltrombopag Olamine

To a solution of ethanolamine (0.9 g) in ethanol (100 mL) was added a solution of 3'-{N'-[1-(3,4-dimethylphenyl)-3-methyl-5-oxo-1,5-dihydro-pyrazol-4-ylidene]hydrazino}-2'-hydroxybiphenyl-3-carboxylic acid (3 g), prepared as in Example 4, in tetrahydrofuran (40 mL) at about room temperature over about 30 to 40 minutes and stirred for about 3 hours at about room temperature. The mixture was filtered, washed with ethanol (25 mL) and dried in an oven at about 55° C. to about 60° C. for about 12 hours. Yield: 3.7 g IR: 3421, 1637, 1508, 1377, 1347, 1293, 1273, 1255, 1227, 1193, 1117, 1064, 1015, 766, 747 cm$^{-1}$ $^1$H NMR (300 MHz in DMSO-d$_6$): δ 14.81 (brs, 1H), 8.20(s, 1H), 7.77-7.83 (m, 4H), 7.64-7.67 (d, 2H), 7.32-7.42 (m, 4H), 7.01-7.07 (t, 3H), 6.87 (d, 2H) 3.56(t, 4H), 2.82 (m, 4H), 2.37 (s, 3H), 2.22 (s, 3H), 2.18 (s, 3H).

Example 6

Preparation of 3'-amino-2'-methoxybiphenyl-3-carboxylic acid

A mixture of 3-bromo-2-methoxyaniline (3 g), 3-carboxyphenylboronic acid (2.94 g), bis(triphenylphosphine)palladium(II)chloride [PdCl$_2$(PPh$_3$)$_2$] (0.30 g) and potassium carbonate (5.2 g) in ethanol (100 mL) and water (20 mL) was heated to about reflux temperature and stirred for about 28 hours. The hot mixture was filtered to remove the catalyst. The clear filtrate was concentrated under vacuum. To the residue, water (50 mL) and methanol (50 mL) was added, acidified to pH 3-5 using hydrochloric acid and stirred for about 30 minutes at about room temperature. The slurry was filtered, washed with n-hexane (50 mL) and dried in an oven at about 55° C. to about 60° C. for about 12 hours.

Yield: 1.8 g $^1$H NMR (300 MHz in DMSO-d$_6$): δ 8.08 (s, 1H), 7.89-7.92 (d, 1H), 7.73-7.75 (d, 1H), 7.51-7.56 (t, 1H), 6.87-6.92 (t, 1H), 6.72-6.74 (d, 1H), 6.50-6.53 (d, 1H), 3.27 (s, 3H)

Example 7

Preparation of 3'-{2-[1-(ethoxycarbonyl)-2-oxopropylidene]hydrazino}-2'-methoxybiphenyl-3-carboxylic acid To a solution of 3'-amino-2'-methoxybiphenyl-3-carboxylic acid (5 g) prepared as in Example 6, in hydrochloric acid (8.5 mL) and methanol (90 mL) was added a solution of sodium nitrite (1.41 g in 400 mL of water) at about 0° C. to about 5° C. under stirring. The reaction mixture was stirred for about 15 minutes at about 5° C. Then ethyl acetoacetate (2.7 g) was added and the reaction mixture was stirred for about 15 minutes at about 0° C. to about 5° C. Solid sodium bicarbonate (15 g) and ethanol (30 mL) was added and the reaction mixture was allowed to warm to about room temperature and stirred for about 2 hours. The mixture was filtered, washed with water (50 mL) and dried under vacuum at about 35° C. to about 40° C. for about 6 hours.

Yield: 4.2 g; Mass: m/z 383.15 [M−1]

$^1$H NMR (300 MHz in DMSO-d$_6$): δ 14.74 (s, 1H), 12.56 (s, 1H), 8.14 (s, 1H), 7.97-8.00 (d, 1H), 7.83-7.85 (d, 1H), 7.60-7.71 (m, 2H), 7.26-7.34 (m, 1H), 7.19-7.23 (m, 1H), 4.10-4.34 (m, 2H), 3.40 (s, 3H), 2.52 (s, 3H), 1.32 (t, 3H)

Example 8

Preparation of 3'-{N'-[1-(3,4-dimethylphenyl)-3-methyl-5-oxo-1,5-dihydro-pyrazol-4-ylidene]hydrazino}-2'-methoxybiphenyl-3-carboxylic acid A solution of 3'-{2-[1-(ethoxycarbonyl)-2-oxopropylidene]hydrazino}-2'-methoxybiphenyl-3-carboxylic acid (3.5 g) prepared as in Example 7, and 3,4-dimethylphenylhydrazine hydrochloride (1.72 g) and sodium acetate(0.9 g) in glacial acetic acid (120 mL) was stirred and heated to about reflux temperature for about 4 hours. The mixture was cooled to about room temperature and stirred for about 1 hour. It was filtered, washed with water (25 mL) and dried in an oven at about 55° C. to about 60° C. for about 12 hours to an orange solid.

Yield: 2.5 g; Mass: m/z 455.61 [M−1]

$^1$H NMR (300 MHz in DMSO-d$_5$): δ 13.75 (brs, 1H), 8.17 (s, 1H), 7.99-8.01 (d, 1H), 7.84-7.87 (d, 1H), 7.64-7.79 (d, 1H), 7.62-7.67 (t, 1H), 7.34-7.40 (t, 1H), 7.27-7.29 (d, H), 7.19-7.22 (d, 1H), 3.34 (s, 3H), 2.32 (s, 3H), 2.26 (s, 3H), 2.22 (s, 3H)

Example 9

Preparation of 3'-{2-[1-(ethoxycarbonyl)-2-oxopropylidene]hydrazino}-2'-methoxybiphenyl-3-carboxylic acid A mixture of ethyl-2-[(3-bromo-2-methoxyphenyl)hydrazono]-3-oxobutanoate (4 g) prepared as in Example 1, 3-carboxyphenylboronic acid (2.30 g), bis(triphenylphosphine)palladium(II)chloride [PdCl$_2$(PPh$_3$)$_2$] (0.30 g), potassium carbonate (4.023 g) in ethanol (100 mL) and water (30 mL) was heated to about reflux temperature and stirred for about 20 hours. The hot mixture was filtered to remove the catalyst. The clear filtrate was concentrated under vacuum. To the residue, water (100 mL) was added, acidified to pH 3-5 using hydrochloric acid and stirred for about 30 minutes at about room temperature. The slurry was filtered, washed with water (25 ml) and dried in an oven at about 55° C. to about 60° C. for about 12 hours.

Yield: 1.9 g: Mass: m/z 383.15 [M−1]

1H NMR (300 MHz in CDCl$_1$): δ 13.7 (brs, 1H), 8.36 (s, 1H), 8.13-8.16 (d, 1H), 7.88-7.91 (d, 1H), 7.68-7.71 (d, 1H), 7.55-7.60 (m, 1H), 7.24-7.29 (m, 1H), 7.15-7.18 (d, 1H), 4.36-4.44 (m, 2H), 3.49 (s, 3H), 2.62 (s, 3H), 1.41 (t, 3H)

Example 10

Preparation of 1-(3,4-dimethylphenyl)-3-methyl-4-(3-bromo-2-hydroxyphenyl)hydrazono-5-pyrazolone A solution of 1-(3,4-dimethylphenyl)-3-methyl-4-(3-bromo-2-methoxyphenyl)hydrazono-5-pyrazolone(5 g) prepared as in Example 2, in 48% aqueous hydrobromic acid (200 mL) and glacial acetic acid (50 mL) was stirred and heated under reflux for about 80 hours. The reaction mixture was concentrated under vacuum to obtain a thick residue. Water (40 mL) was added and basified to pH 7-8 using saturated solution of sodium bicarbonate (20 mL). The mixture was filtered to give an orange solid, which was washed with water (25 mL) and dried in an oven at about 55° C. to about 60° C. for about 12 hours. Yield: 3.5 g $^1$H NMR (300 MHz in DMSO-d$_6$): δ 13.45 (brs, 1H), 10.98 (brs, 1H), 7.69-7.71 (d, 1H), 7.59-7.62 (d, 2H), 7.12-7.21 (m, 2H), 6.92-6.95 (d, 1H), 2.31 (s, 3H), 2.26 (s, 3H), 2.22 (s, 3H)

Example 11

Preparation of 3'-{N'-[1-(3,4-dimethylphenyl)-3-methyl-5-oxo-1,5-dihydro-pyrazol-4-ylidene]hydrazino}-2'-hydroxybiphenyl-3-carboxylic acid A mixture of 1-(3,4-dimethylphenyl)-3-methyl-4-(3-bromo-2-hydroxyphenyl)hydrazono-5-pyrazolone (2 g) prepared as in Example 10, 3-carboxyphenylboronic acid (1 g), bis(triphenylphosphine)palladium(II)chloride [PdCl$_2$(PPh3)$_2$] (0.2 g), potassium hydroxide (1.50 g) in ethanol (50 mL) and water (20 mL) was heated to about reflux temperature and stirred for about 20 hours. The hot mixture was filtered to remove the catalyst. The clear filtrate was concentrated under vacuum. To the residue, water (100 mL) was added, acidified to pH 3-5 using hydrochloric acid and stirred for about 30 minutes at about room temperature. The slurry was filtered to give an orange solid, which was washed with water (20 mL) and dried in an oven at about 55° C. to about 60° C. for about 12 hours.

Yield: 1.8 g; Melting point: 231.6-232.9° C.; Mass: m/z 443.16 [M+1]

IR: 3292, 1707, 1541, 1503, 1223, 1118, 1000 cm$^{-1}$ $^1$H NMR (300 MHz in DMSO-d$_6$): δ 13.75 (brs, 1H), 13.09 (brs, 1H), 9.69 (s, 1H), 8.13 (s, 1H), 7.94-7.97 (d, 1H), 7.79-7.82 (d, 1H), 7.62-7.71 (m, 3H), 7.16-7.21 (m, 3H), 2.32 (s, 3H), 2.26 (s, 3H), 2.22 (s, 3H)

Example 12

Preparation of Eltrombopag Olamine

To a mixture of 3'-{N'-[1-(3,4-dimethylphenyl)-3-methyl-5-oxo-1,5-dihydro-pyrazol-4-ylidene]hydrazino}-2'-hydroxybiphenyl-3-carboxylic acid (2 g) in water (40 mL), ethanolamine (2.5 g) was added and heated to about reflux temperature for about 2 hours. The mixture was cooled to about 0° C. to about 10° C. and stirred for about 1 hour. The reaction mixture was filtered, washed with water (10 mL) and dried in an oven at about 55° C. to about 60° C. for about 12 hours to get purple solid.

Yield: 1.8 g; Melting point: 237.3-237.6° C.

IR: 3421, 1637, 1508, 1377, 1347, 1293, 1273, 1255, 1227, 1193, 1117, 1064, 1015, 766, 747 cm$^{-1}$ $^1$H NMR (300 MHz in DMSO-d$_6$): δ 14.81 (brs, 1H), 8.20 (s, 1H), 7.77-7.83 (m, 4H), 7.64-7.67 (d, 2H), 7.32-7.42 (m, 4H), 7.01-7.07 (t, 3H), 6.87 (d, 2H) 3.56(t, 4H), 2.82 (m, 4H), 2.37 (s, 3H), 2.22 (s, 3H), 2.18 (s, 3H)

Example 13

Preparation of Eltrombopag Olamine

A mixture of 3'-{N'-[1-(3,4-dimethylphenyl)-3-methyl-5-oxo-1,5-dihydro-pyrazol-4-ylidene]hydrazino}-2'-hydroxybiphenyl-3-carboxylic acid (2 g) and ethanolamine (10 mL) was heated at about 55° C. to about 60° C. for 2 hours. The mixture was cooled to about room temperature and stirred for about 1 hour. It was filtered, washed with ethanol (10 mL) and dried in an oven at about 55° C. to about 60° C. for about 12 hours to get purple solid. Yield: 1.7 g; Melting point: 237.3-237.6° C.

IR: 3421, 1637, 1508, 1377, 1347, 1293, 1273, 1255, 1227, 1193, 1117, 1064, 1015, 766, 747 cm$^{-1}$ $^1$H NMR (300 MHz in DMSO-d$_6$): δ 14.81 (brs, 1H), 8.20 (s, 1H), 7.77-7.83 (m, 4H), 7.64-7.67 (d, 2H), 7.32-7.42 (m, 4H), 7.01-7.07 (t, 3H), 6.87 (d, 2H) 3.56(t, 4H), 2.82 (m, 4H), 2.37 (s, 3H), 2.22 (s, 3H), 2.18 (s, 3H)

Example 14

Preparation of Eltrombopag Olamine a) Preparation of Eltrombpag-Aluminium Complex A mixture of 3'-{N'-[1-(3,4-dimethylphenyl)-3-methyl-5-oxo-1,5-dihydro-pyrazol-4-ylidene]hydrazino}-2'-methoxybiphenyl-3-carboxylic acid (10 g) and aluminium chloride (20.4 g) in toluene (50 mL) was stirred for about 40 hours at about room temperature under nitrogen atmosphere. The reaction mass was poured into dilute hydrochloric acid (100 mL) at about 10° C. to about 15° C. The mixture was filtered to give a solid, which was washed with toluene (20 mL) and dried under vacuum.

IR: 3418, 2924, 1588, 1490, 1407, 1349, 1288, 1172, 1123, 1072, 744,603 cm-1

$^1$H NMR (300 MHz in DMSO-d$_6$): 13 (brs, 1H), 8.57 (s, 1H), 8.0-8.02 (d, 1H), 7.88-7.91 (d, 1H), 7.54-7.63 (m, 4H), 7.41-7.44 (d, 1H), 7.23-7.26 (d, 1H), 6.80-6.85 (t, 1H), 2.33 (s, 3H), 2.28 (s, 3H), 2.25 (s, 3H)

Aluminum content: 3.52% by W/W b) Preparation of Eltrombopag

The above solid cake was added in tetrahydrofuran (100 mL), acetic acid (50 mL) and water (30 mL). The reaction mixture was heated to about reflux temperature and stirred for about 6 hours. The reaction mixture was cooled to about room temperature and 20% sodium chloride solution (50 mL) was added to it. The reaction mass was stirred and the two layers were separated. The organic layer contained the title compound.

c) Preparation of Eltrombopag Ammonium Salt

25% aqueous ammonia (150 mL) was added to the above organic layer and stirred for about 2 hours at about room temperature. The mixture was filtered to give a solid which was washed with water (20 mL) and dried under vacuum.

Yield: 7 g; HPLC Purity: 97.91%

IR: 3368, 3155, 1648, 1546, 1501, 1399, 1382, 1343, 1268, 1226, 1193, 1156, 1053, 1002, 790, 767, 741 cm$^{-1}$ $^1$H NMR (300 MHz in DMSO-d$_6$): δ 14.81 (brs, 1H), 8.17 (s, 1H), 7.80-7.82(m, 3H), 7.65-7.68 (d, 1H), 7.34-7.42 (m, 2H), 7.01-7.07 (m, 2H), 6.87 (t, 1H), 2.37 (s, 3H), 2.22 (s, 3H), 2.18 (s, 3H)

Ammonia content: 4.7% by W/W d) Preparation of Eltrombopag Olamine

To the above solid cake, ethanolamine (50 mL) was added and stirred at about room temperature for about 2 hours. Ethanol (200 mL) was then added to the reaction mixture. The reaction mixture was stirred and filtered to give eltrombopag olamine as a solid, which was washed with ethanol (20 mL) and dried in vacuum oven at about 55° C. to about 60° C. for about 12 hours. Yield: 8 g IR: 3421, 1637, 1508, 1377, 1347. 1293, 1273, 1255, 1227, 1193, 1117, 1064, 1015, 766, 747 cm$^{-1}$ $^1$H NMR (300 MHz in DMSO-d$_6$): δ 14.81 (brs, 1H), 8.20(s; 1H), 7.77-7.83 (m, 3H), 7.64-7.67 (d, 1H), 7.32-7.42 (m, 2H), 7.01-7.07 (t, 2H), 6.87 (m, 1H) 3.56(t, 4H), 2.82 (m, 4H), 2.37 (s, 3H), 2.22 (s, 3H), 2.18 (s, 3H)

Example 15

Preparation of 3-bromo-2-methoxyaniline hydrochloride

To a stirred solution of 3-bromo-2-methoxyaniline (10 g) in ethyl acetate (100 mL) was added concentrated hydrochloric acid (7 mL) at about room temperature. The reaction mixture was stirred for about 2 hours and filtered to give a solid, which was washed with ethyl acetate and dried at about 50° C. to about 55° C. Yield: 10 g Example 16

Preparation of Ethyl 2-[(3-bromo-2-methoxyphenyl) hydrazono]-3-oxobutanoate

To a solution of 3-bromo-2-methoxyaniline hydrochloride (10 g) prepared as in Example 15, in hydrochloric acid (13.5 mL of concentrated hydrochloric acid in 136.5 mL of water) was added a solution of sodium nitrite (3.47 g in 10 mL of water) at about −5° C. to about 5° C. under stirring. The reaction mixture was stirred for about 1 hour at about −5° C. to about 5° C. Then ethylacetoacetate (6.55 g) was added to the reaction mixture and stirred for about 3 hours at about −5° C. to about 5° C. Sodium bicarbonate and methanol was then added to the reaction mixture. The reaction mixture was stirred at about −5° C. to about 5° C. for about 1 hour. The mixture was filtered to give a solid, which was washed with water and dried at about 50° C. to about 55° C. Yield: 13.3 g Example 17

Preparation of 1-(3,4-dimethylphenyl)-3-methyl-4-(3-bromo-2-methoxyphenyl)hydrazono-5-pyrazolone A solution of ethyl-2-[(3-bromo-2-methoxyphenyl)hydrazono]-3-oxobutanoate (10 g) prepared as in Example 15, and 3,4-dimethylphenylhydrazine hydrochloride (6.05 g) and sodium acetate (2.63 g) in acetic acid (150 mL) was stirred and heated to about 80° C. to about 90° C. for about 3 hours. The reaction mixture was cooled to about room temperature and stirred for about 1 hour. The reaction mixture was filtered to give a solid, which was washed with acetic acid. The solid obtained was stirred in water for about 30 minutes at about room temperature, which was then filtered, washed with water and dried at about 55° C. to about 60° C. Yield: 11 g Example 18

Preparation of 3'-{N'-[1-(3,4-dimethylphenyl)-3-methyl-5-oxo-1,5-dihydro-pyrazol-4-ylidene]hydrazino}-2'-methoxybiphenyl-3-carboxylic acid A mixture of 1-(3,4-dimethylphenyl)-3-methyl-4-(3-bromo-2-methoxyphenyl)hydrazono-5-pyrazolone (10 g) prepared as in Example 16, 3-carboxyphenylboronic acid (5.2 g), bis(triphenylphosphine)palladium(II)chloride [PdCl$_2$(PPh$_3$)$_2$] (0.84 g), potassium hydroxide (6.72 g) in ethanol (200 mL) and water (15 mL) was heated to about reflux temperature under nitrogen atmosphere and stirred for about 8 hours. The reaction mixture was cooled to about 30° C. to about 35° C. and stirred for about 4 hours at about the same temperature. The reaction mixture was treated with Norit™ charcoal and filtered over celite bed. The filtrate was treated with EDTA and Scavenger Type 2S. The mixture was stirred at about 30° C. to about 40° C. for about 20 hours and filtered over celite bed. To the filtrate, hydrochloric acid was added to adjust the pH to about 3 to about 5. The mixture was stirred for about 2 hours at about 80° C. to about 85° C. The mixture was cooled to about 40° C. to about 45° C. and filtered. The wet cake was treated with potassium hydroxide in methanol and stirred to give a clear solution. The solution was treated with 50% tributylphosphene in ethyl acetate and stirred for about 20 hours at about room temperature. The pH of the solution was adjusted to about 2 to about 4 using hydrochloric acid and the solid obtained was filtered and purified using tetrahydrofuran. Yield: 9.3 g Example 19

Preparation of Eltrombopag Olamine a) Preparation of Eltrombpag-Aluminium Complex A mixture of 3'-{N'-[1-(3,4-dimethylphenyl)-3-methyl-5-oxo-1,5-dihydro-pyrazol-4-ylidene]hydrazino}-2'-methoxybiphenyl-3-carboxylic acid (10 g) and aluminium chloride (29.3 g) in toluene (50 mL) was stirred for about 30 hours at about room temperature under nitrogen atmosphere. The reaction mass was poured into dilute hydrochloric acid (200 mL) at about 25° C. to about 45° C. The mixture was filtered to give a solid, which was washed with toluene (20 mL) and dried under vacuum.

b) Preparation of Eltrombopag

The above solid cake was added in tetrahydrofuran (200 mL), acetic acid (50 mL) and water (30 mL). EDTA was added to the reaction mixture and the reaction mixture was heated to about 60° C. to about 70° C. and stirred for about 12 hours. The reaction mixture was cooled to about 30° C. to about 40° C. and 15% sodium chloride solution was added to it. The reaction mass was stirred and the two layers were separated. The organic layer was treated with Scavenger Type 2S and 50% tributylphosphene in ethyl acetate, stirred for about 15 hours at about 30° C. to about 40° C. and filtered over celite bed. The filtrate contained the title compound.

c) Preparation of Eltrombopag Ammonium Salt

25% aqueous ammonia (10 mL) was added to the above filtrate at about 30° C. to about 40° C. The mixture was concentrated under vacuum at about 45° C. to about 50° C. The residue obtained was degassed for about 1 hour.

d) Preparation of Eltrombopag Olamine

To the residue, ethanolamine (50 mL) was added and stirred at about 20° C. to about 30° C. for about 2 hours. Methanol was then added to the reaction mixture. The reaction mixture was stirred and filtered to give eltrombopag olamine as solid which was washed with methanol and dried at about 55° C. to about 60° C. Yield: 8 g

The invention claimed is:

1. A process for the preparation of a substituted 3'-hydrazino-biphenyl-3-carboxylic acid compound of formula I and salts thereof,

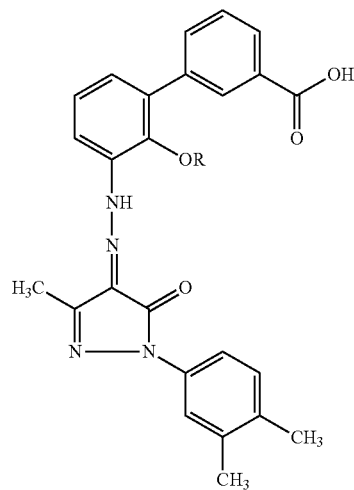

wherein R represents hydrogen, linear or branched $C_{1-6}$ alkyl, $C_{3-8}$ cycloalkyl, optionally substituted benzyl, linear or branched alkylalkoxy, tetrahydrofuranyl, tetrahydropyranyl, medryloxybenzyl, trialkylsilyl, acyl, or trityl; the process comprising:

a) reacting a compound of formula III,

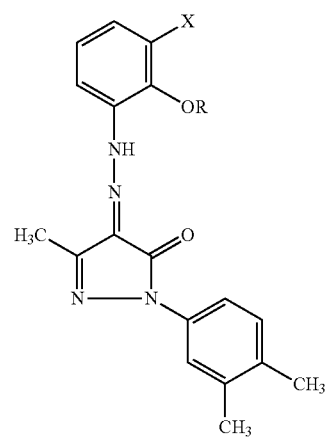

wherein R is as defined above, X is selected from the group consisting of Cl Br, and I, with a compound of formula IV,

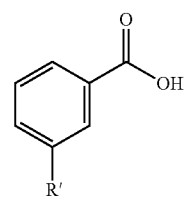

wherein R' represents boronic acid, boronic acid ester or halogen in the presence of a metal catalyst; and (b) optionally, deprotecting the compound of formula I.

2. The process of claim 1, wherein R is $C_{1-6}$ alkyl, X is Br and R' is boronic acid.

3. The process of claim 1, wherein R is $C_{1-6}$ alkyl, X is Br and R' is halogen selected from the group consisting of Cl, Br, and I.

4. The process of claim I, wherein the metal catalyst is selected from the group consisting of $Pd(PPh_3)_4$, $PdCl_2(PPh_3)_2$, $PdCl_2(dppf)$, $Pd(OAc)_2$, $NiCl_2(PPh_3)_2$, and $PdCl_2(dppb)$.

5. A compound of formula III,

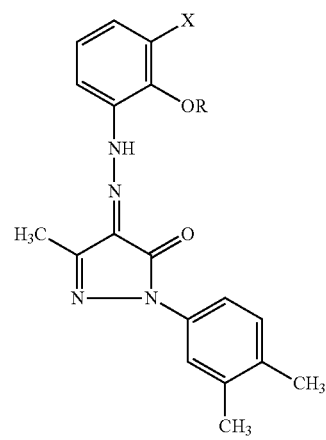

wherein X is selected from the group consisting of Cl, Br, and I and R represents hydrogen, linear or branched $C_{1-6}$ alkyl, $C_{3-8}$ cycloalkyl, optionally substituted benzyl linear or branched alkylalkoxy, tetrahydrofuranyl, tetrahydropyranyl, methyloxybenzyl trialkylsilyl, acyl, or trityl.

6. The compound of claim 5, wherein X is Br and R is methyl.

7. The process of claim 1, wherein the compound of formula III is obtained by reacting a compound of formula V,

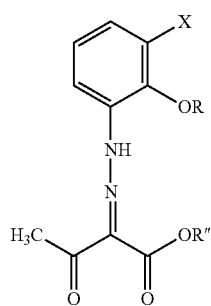

V wherein X is selected from the group consisting of Cl, Br, and I, R represents hydrogen, linear or branched $C_{1-6}$ alkyl, $C_{3-8}$ cycloalkyl optionally substituted benzyl, linear or branched alkylalkoxy, tetrahydrofuranyl, tetrahydropyranyl, methyloxybenzyl, trialkylsilyl, acyl, or trityl and R" represents hydrogen, or a $C_{1-6}$ alkyl, with 3,4-dimethylphenylhydrazine or salt thereof to give the compound of formula III.

8. The process of claim 7, wherein X is Br, R is methyl and R" is ethyl.

9. The process of claim 7, wherein the compound of formula V is obtained by reacting a compound of formula VI or its salt thereof,

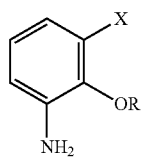

VI wherein X is selected from the group consisting of Cl, Br, and I and R represents hydrogen, linear or branched $C_{1-6}$ alkyl, $C_{3-8}$ cycloalkyl, optionally substituted benzyl linear or branched alkylalkoxy, tetrahydrofuranyl, tetrahydropyranyl, methyloxybenzyl, trialkylsilyl, acyl, or trityl, with alkyl acetoacetate or acetoacetic acid in the presence of an alkali or alkaline earth metal nitrite and an inorganic acid in a solvent system to yield the compound of formula V.

10. The process of claim 9, wherein the inorganic acid is selected from the group consisting of hydrochloric acid, nitric acid, and sulfuric acid.

11. The process of claim 9, wherein the solvent system is selected from the group consisting of methanol, ethanol, water and mixtures thereof.

12. The process of claim 1, for the preparation of eltrombopag, a compound of formula Ia,

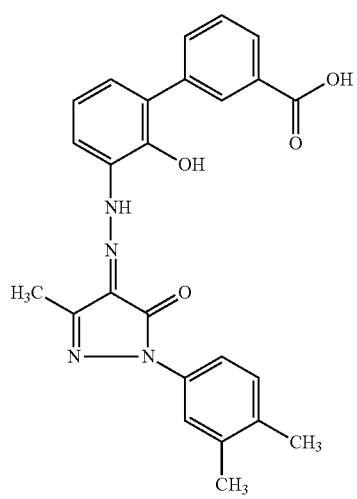

Ia the process comprising subjecting the compound of formula I to a deprotection reaction,

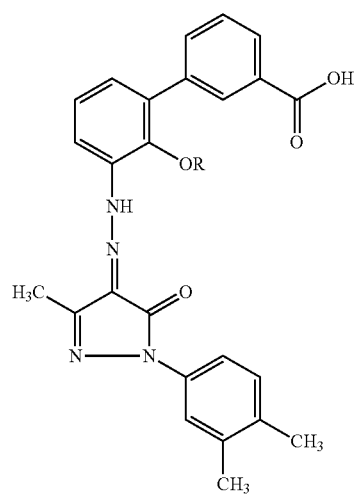

I wherein R has the aforestated meaning.

13. The process of claim 12, herein the deprotection reaction process includes any of the following:
  (a) where R is $C_{1-6}$ alkyl, $C_{3-8}$ cycloalkyl, the deprotection of the compound of formula I is performed using a protic acid; a sulphur compound; or an alkali organomide; or
  (b) where R is substituted benzyl, methyloxybenzyl, the deprotection of the compound of formula I is performed via hydrogenation reaction using hydrogen in the presence of a metal catalyst; or (c) where R is linear or branched alkylalkoxy, tetrahydrofuranyl, tetrahydromanyl, or trilyi, the deprotection of the compound of formula I is performed using an inorganic acid selected from the group consisting of hydrochloric acid, hydrobromic acid, sulfuric acid, and phosphoric acid; or an organic acid; or (d) where R is trialkylsityl, the deprotection of the compound of formula I is performed using an organic acid; or (e) where R is acyl, the deprotection of the compound of formula I is performed using an inorganic acid selected from the group consisting of hydrochloric acid, hydrobromic acid, sulfuric acid, and phosphoric acid; or an inorganic, base selected from the group consisting of sodium hydroxide, potassium hydroxide, sodium carbonate, and potassium carbonate.

14. The process of claim 12, further comprising reacting eltrombopag or a salt thereof with an excess of ethanolamine without using any additional reactor solvent.

15. The process of claim 14, wherein the salt is eltrombopag ammonium salt.

16. The process of claim 1, for the preparation of the compound of formula Ib,

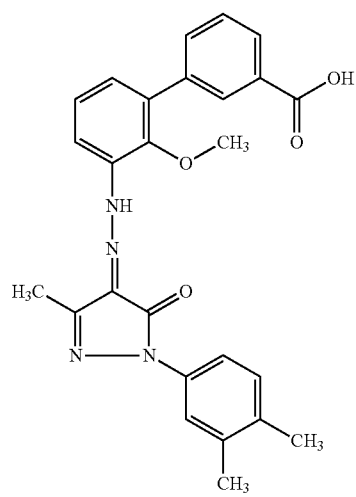

the process comprising reacting the compound of formula III, wherein X is Br and R is methyl, with the compound of formula IV, wherein R' is boronic acid, in the presence of a metal catalyst.

17. The process of claim 16, further comprising deprotecting the compound of formula Ib using a Lewis acid to give eltrombopag, a compound of formula Ia

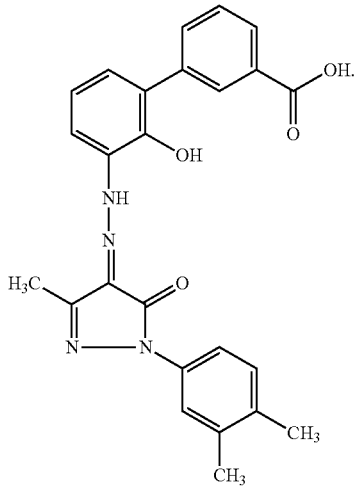

18. The process of claim 17, wherein the Lewis acid is selected from the group consisting of aluminium chloride, aluminium bromide, aluminium iodide, stannous chloride, stannous bromide, titanium chloride, boron trifluoride, boron tribronaide, boron trifluoride-dimethylsulfide complex, beryllium chloride, beryllium bromide, zinc chloride, zinc bromide, trimethylsilylchloride, trimethylsilylbromide, and trimethylsilyliodide.

19. The process of claim 1, wherein the deprotection reaction process includes any of the following:

(a) where R is $C_{1-6}$ alkyl, or $C_{3-8}$ cycloalkyl, the deprotection of the compound of formula I is performed using a probe acid; a Lewis acid; a sulphur compound; or an alkali organomide; or (b) where R is optionally substituted benzyl, methyloxybenzyl, the deprotection of the compound of formula I is performed via hydrogenation reaction using hydrogen in the presence of a metal catalyst; or (c) where R is linear or branched alkylalkoxy, tetrahydrofuranyl, tetrahydropyranyl, or trityl, the deprotectton of the compound of formula I is performed using an inorganic acid or an organic acid; or (d) where R is trialkylsilyl, the deprotection of the compound of formula I is performed using an organic acid; or (e) where R is acyl, the deprotection of the compound of formula I is performed using an inorganic acid selected from the group consisting of hydrochloric acid, hydrobromic acid, sulfuric acid, and phosphoric acid; or an inorganic base selected from the group consisting of sodium hydroxide, potassium hydroxide, sodium carbonate, and potassium carbonate.

* * * * *